United States Patent
Schultz et al.

(10) Patent No.: US 10,810,951 B2
(45) Date of Patent: *Oct. 20, 2020

(54) ELECTROWETTING CELLS WITH HIGH TRANSMISSIVITY FLUIDS

(71) Applicant: ABL IP HOLDING LLC, Conyers, GA (US)

(72) Inventors: Alexander Jacob Schultz, Sterling, VA (US); John M Reilly, Leesburg, VA (US)

(73) Assignee: ABL IP HOLDING LLC, Conyers, GA (US)

(*) Notice: Subject to any disclaimer, the term of this patent is extended or adjusted under 35 U.S.C. 154(b) by 254 days.

This patent is subject to a terminal disclaimer.

(21) Appl. No.: 15/887,219

(22) Filed: Feb. 2, 2018

(65) Prior Publication Data

US 2019/0244574 A1    Aug. 8, 2019

(51) Int. Cl.
*G02B 1/06* (2006.01)
*G09G 3/34* (2006.01)
(Continued)

(52) U.S. Cl.
CPC ........ *G09G 3/348* (2013.01); *B01L 3/50273* (2013.01); *B01L 3/502707* (2013.01);
(Continued)

(58) Field of Classification Search
CPC ........ G02B 19/0014; G02B 3/14; G02B 1/06; G02B 26/005; G02B 3/12
See application file for complete search history.

(56) References Cited

U.S. PATENT DOCUMENTS

| | | | |
|---|---|---|---|
| 2007/0179200 A1* | 8/2007 | Liogier D'Ardhuy | G02B 26/005 516/9 |
| 2016/0201699 A1 | 7/2016 | Heikenfeld et al. | |

(Continued)

OTHER PUBLICATIONS

U.S. Appl. No. 15/674,040, filed Aug. 10, 2017, entitled "Electrowetting Cell Constructs", 55 pages.
(Continued)

*Primary Examiner* — Joseph P Martinez
(74) *Attorney, Agent, or Firm* — RatnerPrestia

(57) ABSTRACT

The examples relate to various implementations of an electrowetting cell and optical devices including the electrowetting cell. The electrowetting cell includes a conductive fluid and a non-conductive fluid having refractive indices that differ by at least 0.2. In an example, the fluids of the electrowetting cell are capable of providing at least 50% transmissivity to radiation in a preselected band within the x-ray, ultraviolet, visible, infrared, microwave, or radiowave spectrums after 1 hour at a temperature of 40° C. and/or after 1 hour of an exposure at an average illuminance of at least 80,000 lux. In another example, the non-conductive fluid is selected from a compound of Formula 1, 2, or 3:

(Formula 1)

(Formula 2)

(Continued)

-continued

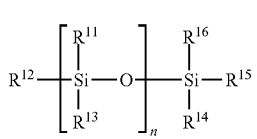
(Formula 3)

in which $R^1$ to $R^9$ and $R^{11}$ to $R^{16}$ are independently selected from H, a saturated or unsaturated, branched or linear C1 to C6 alkyl group, and a phenyl group; R and $R^{10}$ are aromatic groups, optionally substituted by one or more heteroatoms selected from N, O, and Si, and, in Formula 1, $R^1$ and R are optionally linked to one another so as to define a ring; and n is an integer from 1 to 5. The electrowetting cell may be coupled to an optical device, such as a light sensor or light emitting device.

20 Claims, 7 Drawing Sheets

(51) Int. Cl.
| | |
|---|---|
| *B01L 3/00* | (2006.01) |
| *C12M 3/06* | (2006.01) |
| *G02B 26/00* | (2006.01) |
| *G02B 3/12* | (2006.01) |
| *G02B 3/14* | (2006.01) |

(52) U.S. Cl.
CPC ....... *B01L 3/502761* (2013.01); *C12M 23/16* (2013.01); *G02B 1/06* (2013.01); *G02B 3/12* (2013.01); *G02B 3/14* (2013.01); *G02B 26/005* (2013.01); *B01L 2300/0861* (2013.01); *B01L 2300/165* (2013.01); *B01L 2400/0427* (2013.01)

(56) References Cited

U.S. PATENT DOCUMENTS

| | | |
|---|---|---|
| 2017/0018214 A1 | 1/2017 | Black et al. |
| 2017/0045203 A1 | 2/2017 | Mao et al. |
| 2018/0039070 A1 | 2/2018 | Mao et al. |
| 2018/0180256 A1 | 6/2018 | Mao et al. |

OTHER PUBLICATIONS

U.S. Appl. No. 15/479,857, filed Apr. 5, 2017, entitled "Electrowetting Assembly Technique and Cell Structure", 72 pages.
U.S. Appl. No. 15/661,742, filed Jul. 27, 2017, entitled "Sealing and Lateral Pressure Compensation Structures Usable with Fluidic or Gaseous Material Containers", 71 pages.
Notice of Allowance for U.S. Appl. No. 15/887,104, dated Jun. 15, 2020, 9 pages.

\* cited by examiner

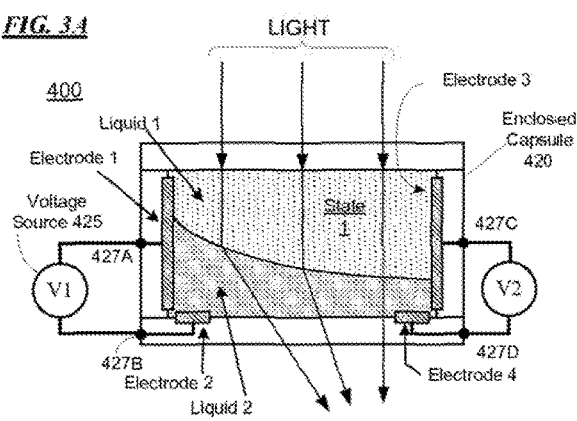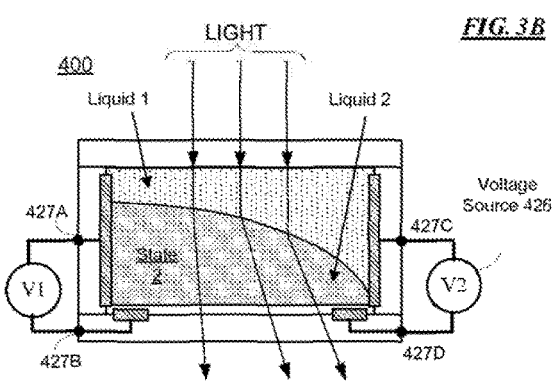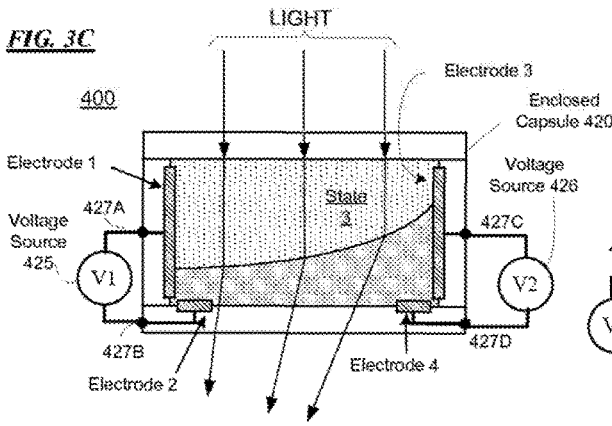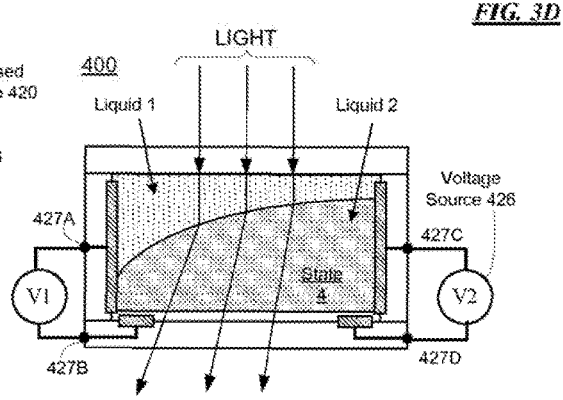

ELECTROWETTING CELLS WITH HIGH TRANSMISSIVITY FLUIDS

TECHNICAL FIELD

The disclosed subject matter relates to electrowetting cells, and to configurations and/or operations thereof, having a high transmissivity.

BACKGROUND

Electrowetting is a microfluidic phenomenon that modifies the shape of a liquid in relation to a surface by applying an electrical field, e.g. by applying a voltage across two electrodes. For example, if the surface is hydrophobic, the electrical field causes a change in the shape of the liquid that appears to change the wetting properties of the hydrophobic surface. Electrowetting cells have a well containing one or more fluids, including a conductive fluid.

If the fluid(s) in an electrowetting cell and some of the wall(s) around the fluid(s) are sufficiently transparent, the electrowetting cell may be used as an electrically controllable optic. Such optics have recently been the subject of a widening scope of light processing applications, such as variable lenses, variable prisms, optical switches, displays, etc.

Electrowetting lenses provide controllable beam shaping. An electrowetting cell may have various different shaped structures, e.g., round, square or rectangular. The overall working principle for either beam shaping or steering is the same—the voltage applied across the dielectric layer attracts or repels the conducting fluid so as to change the wetting area of the cell and thus the shape of the fluid(s) in the cell.

Over time, optical clarity of the fluid(s) in an electrowetting cell can diminish, for example, when used in long duration applications involving high intensity light or high temperatures. The fluid(s) can become hazy or discolor, reducing the amount of radiation, e.g. light, that passes through the electrowetting cell. Haziness can occur, for example, when solid particles form in the fluids, diffusing the radiation passing through the cell. Discoloration can change the color output of a light source or, if the electrowetting cell is used with an image sensor, can alter the radiation incident on the sensor. While not wishing to be bound by theory, it is believed that the fluid(s) can break down over time or when exposed to high heat or radiation flux. Alternatively, the conductive fluid may react with a non-conductive fluid.

There is a need in the art for electrowetting cells that address one or more of these issues.

SUMMARY

The concepts disclosed herein improve over the art by providing electrowetting cells that may maintain high transmissivity of radiation.

The detailed description below and the accompanying drawings disclose examples of electrowetting cells and optical devices comprising electrowetting cells. In such an example, an electrowetting cell in this example comprises a conductive fluid and a non-conductive fluid having refractive indices that differ by at least 0.2. The fluids of the electroetting cell are capable of providing at least 50% transmissivity with regard to light in a preselected band within the ultraviolet, visible, or infrared spectrums after 1 hour at a temperature of 40° C. and/or after 1 hour of an exposure at an average illuminance of at least 80,000 lux.

In some examples, a light device includes a light source and an electrowetting cell coupled to the light source. The electrowetting cell in this example comprises a conductive fluid and a non-conductive fluid having refractive indices that differ by at least 0.2. The fluids of the electrowetting cell are capable of providing at least 50% with regard to light in a preselected band within the ultraviolet, visible, or infrared spectrums after 1 hour at a temperature of 40° C. and/or after 1 hour of an exposure at an average illuminance of at least 80,000 lux.

In other examples, a light device includes a light source and an electrowetting cell coupled to the light source. The electrowetting cell in this example comprises a conductive fluid and a non-conductive fluid having refractive indices that differ by at least 0.2, and the non-conductive fluid is selected from a compound of Formula 1, Formula 2, or Formula 3:

(Formula 1)

wherein:
$R^1$, $R^2$, and $R^3$ are independently selected from H, a saturated or unsaturated, branched or linear C1 to C6 alkyl group, and a phenyl group;
R is an aromatic group optionally substituted by one or more heteroatoms selected from N, O, and Si, wherein in Formula 1, $R^1$ and R are optionally linked to one another so as to define a ring;

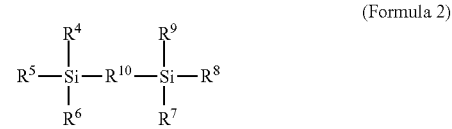
(Formula 2)

wherein:
$R^4$, $R^5$, $R^6$, $R^7$, $R^8$, and $R^9$ are independently selected from H, a saturated or unsaturated, branched or linear C1 to C6 alkyl group, and a phenyl group;
$R^{10}$ is an aromatic group optionally substituted by one or more heteroatoms selected from N, O, and Si; and

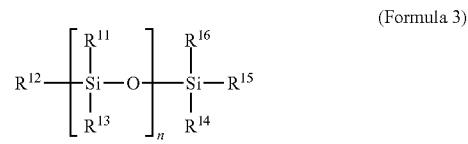
(Formula 3)

wherein:
$R^{11}$, $R^{12}$, $R^{13}$, $R^{14}$, $R^{15}$, and $R^{16}$ are independently selected from H, a C1 to C6 alkyl group, and a phenyl group; and
n is an integer from 1 to 5, wherein when n is 2 to 5, each $R^{11}$ and $R^{13}$ group may be the same or different.

Some examples include an electrowetting cell comprising a conductive fluid and a non-conductive fluid having refractive indices that differ by at least 0.2. The fluids of the electrowetting cell are capable of providing at least 50% transmissivity with regard to radiation in a preselected band within the x-ray, ultraviolet, visible, infrared, microwave, or radiowave spectrums after 1 hour at a temperature of 40° C. and/or after 1 hour of an exposure at an average illuminance of at least 80,000 lux.

Other examples include an electrowetting cell comprising a conductive fluid and a non-conductive fluid having refractive indices that differ by at least 0.2, and the non-conductive fluid is selected from a compound of Formula 1, Formula 2, or Formula 3:

(Formula 1)

wherein:

$R^1$, $R^2$, and $R^3$ are independently selected from H, a saturated or unsaturated, branched or linear C1 to C6 alkyl group, and a phenyl group;

R is an aromatic group optionally substituted by one or more heteroatoms selected from N, O, and Si, wherein in Formula 1, $R^1$ and R are optionally linked to one another so as to define a ring;

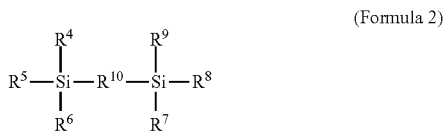
(Formula 2)

wherein:

$R^4$, $R^5$, $R^6$, $R^7$, $R^8$, and $R^9$ are independently selected from H, a saturated or unsaturated, branched or linear C1 to C6 alkyl group, and a phenyl group;

$R^{10}$ is an aromatic group optionally substituted by one or more heteroatoms selected from N, O, and Si; and

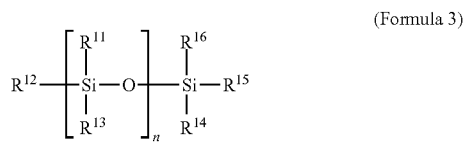
(Formula 3)

wherein:

$R^{11}$, $R^{12}$, $R^{13}$, $R^{14}$, $R^{15}$, and $R^{16}$ are independently selected from H, a C1 to C6 alkyl group, and a phenyl group; and n is an integer from 1 to 5, wherein when n is 2 to 5, each $R^{11}$ and $R^{13}$ group may be the same or different.

Other examples include optical devices comprising an electrowetting cell. The optical devices may include an image sensor, wherein the electrowetting cell is coupled to the image sensor to optically and/or spatially distribute radiation incident on the image sensor. In another example, the optical device may include a light emitting device, wherein the electrowetting cell is coupled to the light emitting device to optically and/or spatially distribute light emitted by the light emitting device.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

FIGS. 3A to 3D are cross-sectional views of an electrowetting cell, in which FIGS. 3A and 3B illustrate a first selected direction of optical steering and two different states of beam shaping, and FIGS. 3C and 3D illustrate a second selected direction of optical steering and two different states of beam shaping.

DETAILED DESCRIPTION

Figure 1:
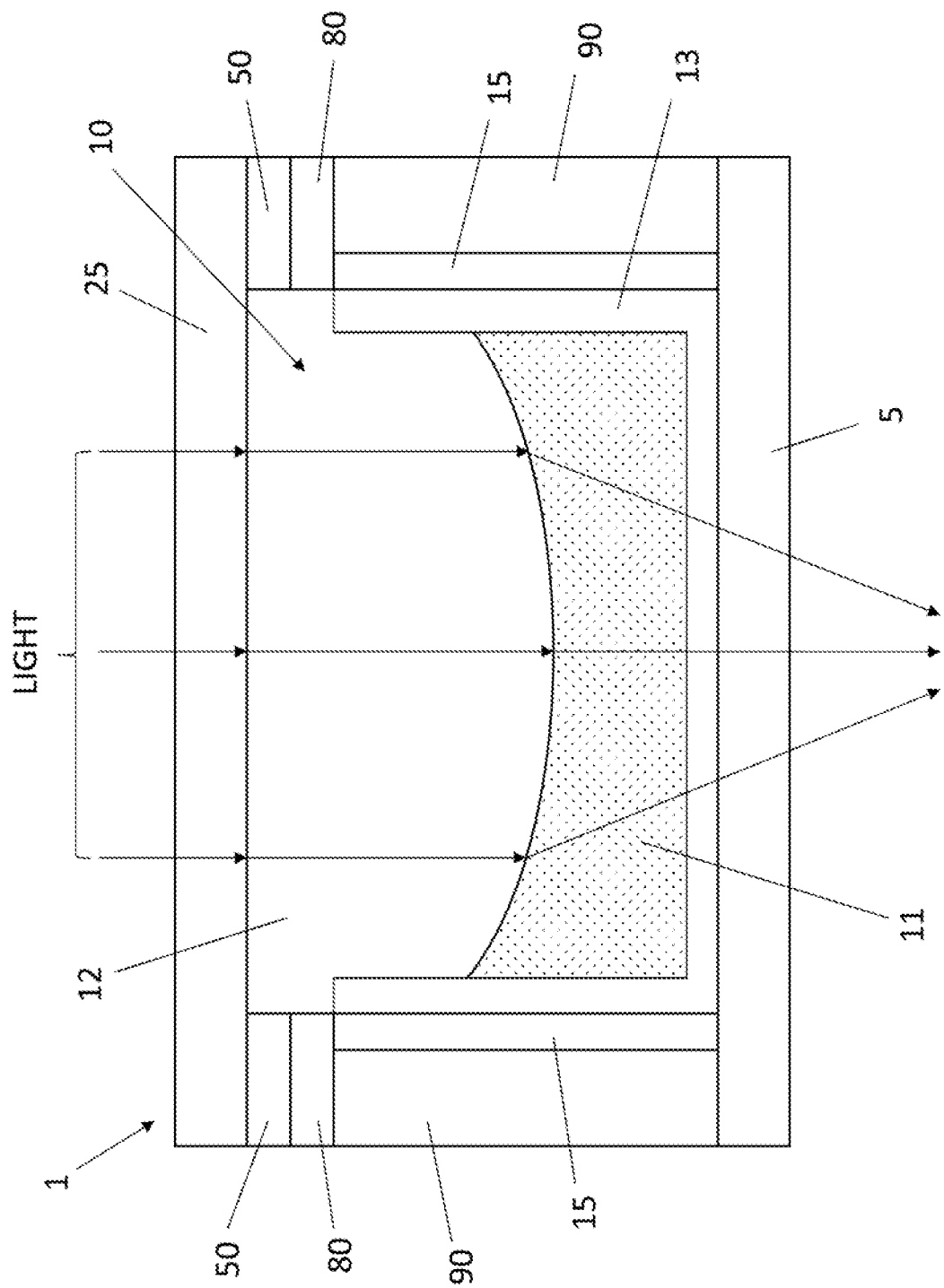
FIG. 1 is a cross-sectional view of an electrowetting cell containing a two-fluid system according.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Electrowetting is a fluidic phenomenon that enables changing of the configuration of a contained fluid system in response to an applied voltage. In general, application of an electric field seemingly modifies the wetting properties of a surface (e.g. the ability of fluid to maintain physical contact with a hydrophobic surface) in the fluid system. Assuming a two fluid system, where one fluid is relatively conductive, and the other is relatively non-conductive; when a fluid is in contact with a surface and that surface becomes charged, the electric field tends to pull the mass of the electrically conductive fluid towards the surface. As the conductive fluid changes shape due to this force, the non-conductive fluid also changes shape. On a micro scale, the contact angle is unaffected. On a macro scale it seems that the wetting properties have changed. This phenomenon enables controlled changes to the overall distribution and shape of the fluids with respect to the surface, in response to changes of the voltage(s) applied to change the electric field.

Examples of electrowetting cells or cell structures are disclosed in U.S. patent application Ser. No. 15/674,040, filed Aug. 10, 2017, entitled "Electrowetting Cell Constructs"; U.S. patent application Ser. No. 15/479,857, filed Apr. 5, 2017, entitled "Electrowetting Assembly Technique and Cell Structure"; and U.S. patent application Ser. No. 15/661,742, filed Jul. 27, 2017, entitled "Sealing and Lateral Pressure Compensation Structures Usable With Fluidic or Gaseous Material Containers," the entire contents of which are incorporated by reference herein.

In a transmissive electrowetting cell example using two fluids, changing the applied electric field changes the shape of the fluid interface surface between the two fluids and thus the refraction of the radiation passing through the interface surface, for example, so that the electrowetting cell operates as a variable shape lens and/or a variable shape prism. Depending on the application for the electrowetting cell, the radiation may enter the fluid system to pass first through either one or the other of the two fluids.

The electrowetting cells disclosed herein may be used with any form of radiation in the electromagnetic spectrum. For example, the electrowetting cells may be used in the optical spectrum ($\lambda$=10 nm-1 mm), including the ultraviolet ($\lambda$=10 nm-400 nm), visible ($\lambda$ =390 nm-750 mm), and infrared ($\lambda$=750 nm-1 mm) spectrums. In other examples, the electrowetting cells may be used with radiation in the x-ray (0.01-10 nm) spectrum, the microwave ($\lambda$=1 mm-0.5 m) spectrum, or the radiowave spectrum (0.5 m-100 km). The electrowetting cells may also be used with radiation within one or more of the various spectra, such as, for example, an electrowetting cell that is used in both the visible and infrared spectrums.

Reference now is made in detail to the examples illustrated in the accompanying drawings and discussed below.

An example of an electrowetting cell 1 containing a two-fluid system is shown in FIG. 1. A well 10 is formed by a first plate 25, a second plate 5, and side walls 90. The cross-section of the well in the direction of the radiation can be circular, elliptical, square, rectangular, or any other desired geometry. Although the radiation is shown entering the electrowetting cell 1 through the first plate 25, the radiation may also enter through second plate 5. In other examples, one of the first plate 25 and the second plate 5 may be reflective such that the light exits the same plate through which it enters.

The two-fluid system comprises a non-conductive fluid 11 and a conductive fluid 12, which are placed in the well 10. Electrodes 15 and 50 are positioned along the well 10. When an electric field is applied to the cell by electrodes 15 and 50, the fluids are deformed and act as a lens. The focus achieved by the deformation of the fluids can be controlled by varying the electric field applied by the electrodes.

In the example shown in FIG. 1, a layer 13 is formed adjacent the side walls 90 and second plate 5. Layer 13 is an optional layer and may comprise a dielectric layer and/or a hydrophobic layer separating the fluids from electrode 15. In FIG. 1, layer 13 is shown covering side walls 90 and second plate 5. In other examples, layer 13 may be formed only over electrode 15.

As commercial applications for electrowetting optics or cells expand, such cells are used in increasing numbers and operating conditions. Increased use and more demanding operating conditions call for more effective and/or efficient electrowetting cells.

One measure of an electrowetting cell's effectiveness or efficiency is the transmissivity, or the ability of the electrowetting cell to transmit radiation as may be desired for a particular application. In two fluid systems, the fluids may interact or react with one another over time. External factors such as heat or radiation flux (e.g. luminous flux) may increase the rate at which the optical clarity or light transmission deteriorates.

The orientations of the electrowetting optics or cells, associated components and/or any complete devices incorporating a cell such as shown in any of the drawings, are given by way of example only, for illustration and discussion purposes. The fluid systems disclosed herein may be used in other electrowetting optics or cells and are not limited to the examples described herein. In operation for a particular variable optical processing application, an electrowetting cell may be oriented in any other direction suitable to the particular application of the cell, for example up light or side light or any other orientation. Also, to the extent used herein, any directional term, such as lateral, longitudinal, up, down, upper, lower, top, bottom and side, are used by way of example only, and are not limiting as to direction or orientation of any optic or component of an optic constructed as otherwise described herein.

The term "coupled" as used herein refers to any logical, optical, physical or electrical connection, link or the like by which signals or light produced or supplied by one system element are imparted to another coupled element. Unless described otherwise, coupled elements or devices are not necessarily directly connected to one another and may be separated by intermediate components, elements or communication media that may modify, manipulate or carry the light or signals.

Examples of electrowetting cells described in detail herein and shown in several of the drawings use two immiscible fluids having different electrical properties. In at least some examples, the two fluids have different indices of refraction. One fluid may be conductive. The other fluid, typically the fluid adjacent to a hydrophobic surface, may be non-conductive. The fluids may be substantially transparent or transmissive, for example, with respect to radiation in a preselected band. In at least some examples, the non-conductive fluid exhibits a higher index of refraction than the conductive fluid. For example, the fluids of the electrowetting cell may have refractive indices that differ by at least 0.2. In some examples, the fluids in the electrowetting cell are capable of providing at least 50% transmissivity with regard to radiation in a preselected band within the x-ray, ultraviolet, visible, infrared, microwave, or radiowave spectrums even after 1 hour of operation at a temperature of 40° C. and/or after 1 hour of an exposure at an average illuminance of at least 80,000 lux. A variety of examples of the fluids are described below. The two fluids may also have a difference in surface tension. For example, the two fluids may have a surface tension that differs by at least 10 mN/m, such as at least 15 mN/m or at least 20 mN/m. In at least one example, the conductive fluid may be a liquid of a type having a surface tension greater than 60 mN/m, and the non-conductive fluid may be a liquid of a type having a surface tension less than 40 mN/m. In some examples, the non-conductive fluid may be selected to more closely match a dielectric layer in the electrowetting cell. Specific formulas and compounds for suitable examples of the non-conducting fluid are described in more detail later.

Before describing further details of examples of the fluids, it may be helpful to consider several additional examples of electrowetting cell structures that may utilize the particular types of fluids.

Figure 2A:
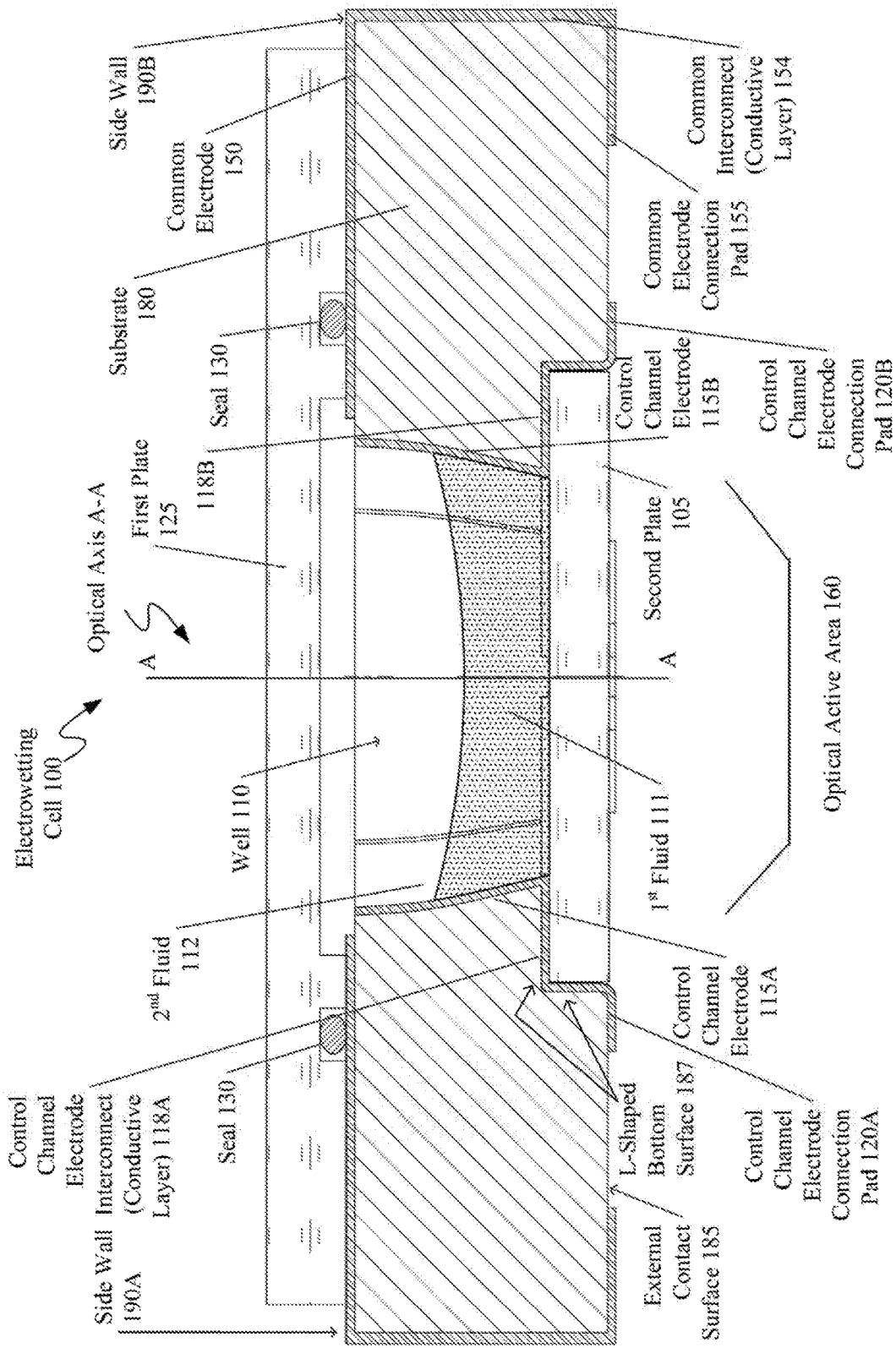
FIG. 2A is a cross-sectional view of parts of an assembled electrowetting cell construct, including a substrate formed of ceramic or fiberglass mesh infused with resin, first and second plates, and conductive layer interconnects for control channel and common electrodes.

FIG. 2A is a cross-sectional view of one exemplary electrowetting cell construct 100. As shown, the electrowetting cell 100 includes a first plate 125, a second plate 105, a substrate 180 formed of ceramic or fiberglass mesh infused with resin, a well 110 in the middle of the substrate 180, control channel electrodes 115A-B, a common electrode 150, and various interconnects that lead to external contact surface 185, for example, that is located outside the well 110 and around at least a portion of one end of the well 110 to provide electrical connection to the electrodes as depicted. In an example, the external contact surface 185 can be located outside of the electrowetting cell 100. In the visible cross-section illustrated in the example, electrowetting cell 100 includes two control channel electrode interconnects 118A-B and a common electrode interconnect 154. Although not completely visible, it should be understood that, in total, there are four control channel electrodes and four respective control channel electrode interconnects, two of which the cross-section intersects. An additional control channel electrode is visible on the back wall of the well 110, and one of the four control channel electrodes is not visible in the depicted cross-section.

Each control channel electrode interconnect 118A-B is connected to a respective control channel electrode 115A-B and a respective control channel electrode connection pad 120A-B. The common electrode interconnect 154 is connected to the common electrode 150 and the common electrode connection pad 155. In the example of FIG. 2A, each of the control channel electrode interconnects 118A-B is a conductive layer deposited on at least one surface of the substrate 180 that leads to a respective control channel electrode connection pad 120A-B to provide electrical connectivity between the respective control channel electrode 115A-B and the respective control channel electrode connection pad 120A-B. The control channel electrodes 115A-B are formed on the side walls of the well 110 to control a shape of different portions of the second fluid 112 in the well 110 in response to applied control voltage. Each of the control channel electrodes 115A-B can be formed of aluminum or other suitable material.

The common electrode interconnect 154 is a conductive layer deposited on at least one surface of the substrate 180 that leads to the common electrode connection pad 155 to provide electrical connectivity between the common electrode 150 and the common electrode connection pad 155. As shown, both side walls 190A-B and the external contact surface 185 of the substrate 180 are plated with conductive layers, such as surface metallization layers.

It should be understood that each of control channel electrodes 115A-B includes a separate control channel electrode interconnect 118A-B as shown in FIG. 2A. Moreover, only one side of the electrowetting cell 110 is shown in the cross-section of FIG. 2A, which intersects control channel electrodes 115A-B and control channel electrode interconnects 118A-B. Although not visible, one additional control channel electrode, two control channel electrode interconnects, and two control channel electrode pads are formed in the example electrowetting cell 100.

Although only the common electrode interconnect 154 to the right side of the well 110 is labeled in FIG. 2A, multiple common electrode interconnects 154 can be formed that lead to the common electrode connection pad 155. Typically, the common electrode connection pad 155 is formed as a single continuous ring around the external contact surface 185. However, the common electrode connection pad 155 can be broken up into several pads depending on the design of the electrowetting cell 100.

In one example, an optical active area 160 may be formed through which light is transmitted or reflected through is formed and includes an optical axis A-A which corresponds to where light passes through the optical active area 160 of the cell 100. The second plate 105 shown on the bottom of the electrowetting cell 100 resides in the optical active area 160 and is a transparent window that can be formed of clear or transparent (e.g., highly light transmissive) glass, plastic (e.g., acrylic), etc. The first plate 125 shown on the top of the electrowetting cell 100 covering the well 110 can be formed of a variety of suitable materials, but the portion of the first plate 125 in the optical active area is also typically formed of clear or transparent glass, plastic, etc.

The well 110 is located inside the substrate 180 and is enclosed by the substrate 180 on the sides, the first plate 125 on the top, and the second plate 105 on the bottom. The well 110 is a hollow chamber filled with at least one fluid and the bottom, top, and sides of the well are enclosed. Generally described, the well 110 is a chamber or vessel that contains fluid(s), gas(es), or both. In an example, the well 110 is formed of the material of the first plate 125 and the second plate 105 on the top and bottom, respectively, and the material of the substrate 180 on side walls of the well 110. The well 110 may be filled with a first non-conductive fluid 111 and a second conductive fluid 112, and the fluids 111 and 112 are immiscible. The fluids are controlled by an electric field that is imparted between the common electrode 150 and the control channel electrodes 115A-B that is based on an applied voltage. The conductive fluid is driven while the shape of the oil is passively modified based on how the water displaces it. However, other fluids or gases can be used to fill the well 110 and various materials can be used to form the well 110, particularly in areas besides the top (e.g., first plate 125) and bottom (e.g., second plate 105) which are typically formed of transparent materials to allow for light transparency.

In the example, the first non-conductive fluid 111 is at the sealed distal end of the well 110 in the volume of the well 110 that is enclosed by the second plate 105 on the bottom and the substrate 180 on the sides. The second conductive fluid 112, fills a remainder of the well 110 at the proximal end of the well 110 in the volume of the well 110 that is enclosed by the first plate 125 on the top and by a seal 130 (e.g., O-ring) on the sides. The fluids 111 and 112 can be installed in the well 110 before installation of the seal 130 or after. Forming the control channel electrode interconnects 118A-B and common electrode interconnect 154 to lead to the external contact surface 185 of the electrowetting cell 100 where the fluids 111 and 112 are not contained allows for robust electrical connections to the control channel electrodes 115A-B and common electrode 150 after the filling process.

The example electrowetting cell construct 100 generally relates to light transmissive electrowetting cells, that is to say cells that act as lenses and/or prisms and are relatively transparent with respect to light that passes entirely through the optically active area of a given cell. Teachings herein may also relate to reflective electrowetting cells. For a reflective cell, a reflector could either be at one end of the well 110. In such a reflective example, the first plate 125 covering the well 110 or the second plate 105 forming the bottom of the well 110 can be reflective instead of transparent material, to provide a reflective electrowetting cell for other types of variable optic applications. Another reflective approach involves forming a reflector at the meniscus forming the interface of the two fluids. Alternatively, one of the fluids may be reflective.

Figure 2B:
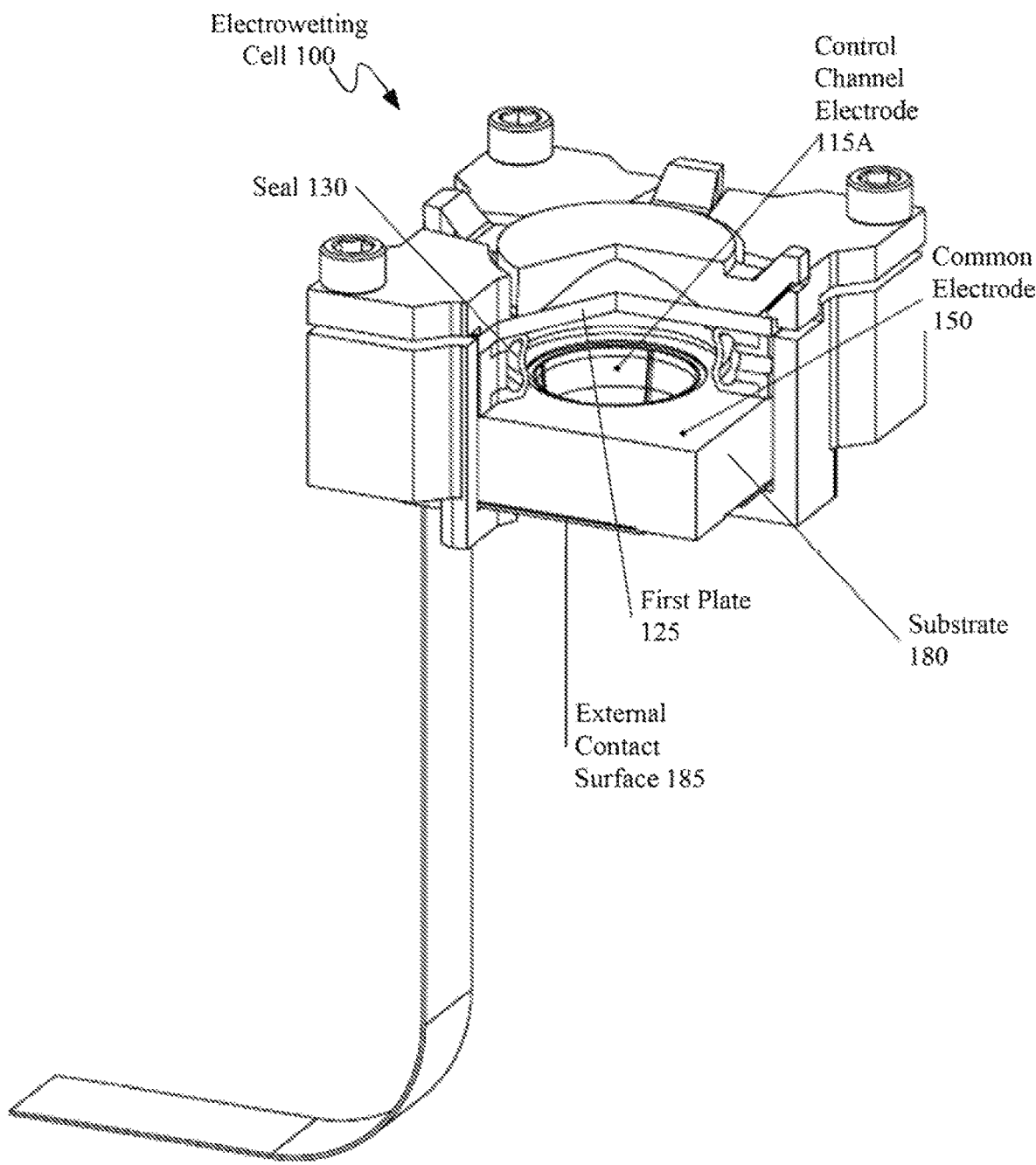
FIG. 2B is a cutaway view of the electrowetting construct of FIG. 2A illustrating the substrate, the first plate, and the control channel and common electrodes.
Figure 2C:
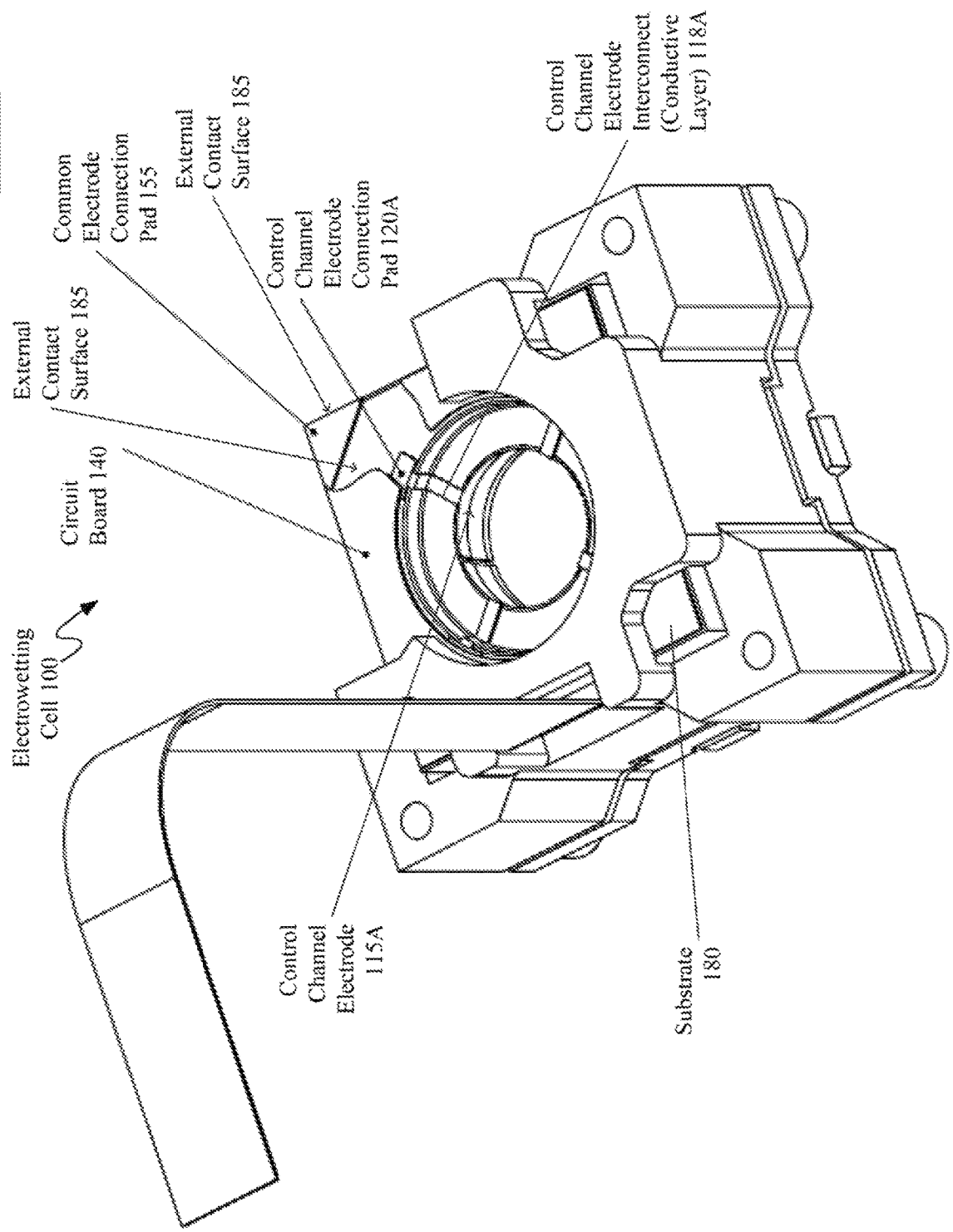
FIG. 2C is a cutaway view of the electrowetting cell construct of FIG. 2A which is upside down relative to FIG. 2B and shows the conductive layer interconnects reaching the control channel electrode and common electrode connection pads.

FIG. 2B is a cutaway view of the first electrowetting construct 100 illustrating the substrate 180, the first plate 125, the control channel electrode 115A, and the common electrode 150. FIG. 2C is also a cutaway view of the first electrowetting cell construct 100, but is upside down relative to FIG. 2B. As shown, the control channel electrode interconnect 118A extends between the control channel electrode 115A and the control channel electrode connection pad 120A to provide electrical connectivity to the control channel electrode 115A through the external contact surface 185 of the electrowetting cell 100. The common electrode connection pad 155 is also shown on the external contact surface 185. A common electrode interconnect (not shown) is formed as a conductive layer deposited on side wall 190A that extends between the common electrode 150 and leads to the common electrode connection pad 155 to provide electrical connectivity between the common electrode 150 and the common electrode connection pad 155 through the external contact surface 185.

As shown in FIG. 2C, a circuit board 140 is coupled to the external contact surface 185 and the circuit board 140 includes various circuit connections. The circuit board circuit connections are in electrical contact with the control channel electrode connection pads 120A-B and the common electrode connection pad 155 to supply a driving voltage to the control channel electrodes 115A-B. The circuit board 140 can be a flexible printed circuit board (PCB) that may include dimples to contact the control channel electrode connection pads 120A-B and common electrode connection pad 155. Dimples are compressible depressed or raised areas that may be upward or downward facing. Alternatively, standard flat pads on the circuit board 140 would connect to the control channel electrode connection pads 120A-B and common electrode connection pad 155. In an example, standard FR4 non-flexible PCB type of circuit board 140 with pads connects to the pads 120A-B and 155 on the external contact surface 185, or a non-flexible PCB type of circuit board 140 with pads and pogo pins or other soldered on components is used to create variable height pressure contacts. In another example, an FR4 type or ceramic substrate 180 is reflowed and populated with connectors or pogo pins, etc. before filling to eliminate the need for a solid or flexible PCB for electrical connections to the substrate 180.

The example in the drawings and described above includes an integrated approach to the construction of an electrowetting cell that incorporates all circuits and connection pads into the cell to form one component. This can be accomplished through a layered circuit board approach using ceramic or fiberglass mesh infused with resin, that accommodates the use of through hole vias, blind vias, and multilayered circuits. This can also be accomplished with a solid substrate using ceramic or fiberglass mesh infused with resin that accommodates the addition of electrical traces, contacts, and vias, for example.

The two fluids 111 and 112 typically exhibit a difference in an optical characteristic, e.g. refractive index. In some examples, the refractive indices of the two fluids differs from at least 0.2, such as, for example, at least 0.25 or at least 0.3. The refractive index may be measured according to ASTM D-1218.

The two fluids 111 and 112 are substantially immiscible with one another. As used herein, the term "substantially immiscible" means that one fluid has limited miscibility in the other fluid. For example, substantially immiscible fluids may have a miscibility of less than 0.2% w/w.

According to some examples, the fluids in the electrowetting cell transmit at least 50% of the light in the visible spectrum (390 nm to 750 nm). Transmittance can be measured, for example, using a spectrophotometer. In other examples, the fluids in the electrowetting cell transmit at least 75% of light in the visible spectrum, at least 80%, at least 85%, at least 90%, or at least 95%.

As described in the examples below, fluid systems conventionally used in electrowetting cells have been observed to have diminishing light transmittance over time. Fluid systems may become hazy or discolor due to reactions or interactions within the fluid system. Haziness can result in reflection or scattering of light when the light hits particles suspended in the fluid system. Discoloration may be caused by the absorption of certain wavelengths of light. Diminished light transmittance may be exacerbated, for example, by exposure of the electrowetting cell to high temperatures or luminous flux.

In at least some examples, the fluids within the electrowetting cell transmit at least 50% of the radiation in the preselected band after being exposed to a temperature of 40° C. for 1 hour. In other examples, the fluids transmit at least 50% of the radiation in the preselected band after being exposed to a temperature of 40° C. for at least 2 hours, for at least 4 hours, for at least 8 hours, for at least 16 hours, for at least 1 day, or for at least 1 week. In some examples, the fluids transmit at least 60% of the radiation in the preselected band after being exposed to a temperature of 40° C. for 1 hour, at least 75%, at least 80%, at least 85%, or at least 90% of the radiation in the preselected band.

In other examples, the fluids within the electrowetting cell transmit at least 50% of the radiation in the preselected band after being exposed to a temperature of 50° C. for 1 hour, at a temperature of 60° C. for 1 hour, or at a temperature of 70° C. for 1 hour.

In some examples, the fluids in the electrowetting cell transmit at least 50% of the radiation in the preselected band after use in expected operating conditions for at least 1 day, such as, for example, at least 60%, at least 75%, at least 80%, at least 85%, or at least 90% of the radiation in the preselected band. In other examples, the fluids in the electrowetting cell transmit at least 50% of the radiation in the preselected band after use in expected operating conditions for at least 3 days, at least 7 days, at least 14 days, or at least 28 days. Expected operating conditions include the radiation flux (e.g., luminous flux) and temperature of the device in operation. Luminous flux may range, for example, from 25 lumens to several hundred lumens, such as 250 lumens, 500 lumens, or more. In use, a lighting device containing the electrowetting cell according to some examples may reach 40° C., 50° C., 60° C., 70° C., or, higher, particularly if the device is used outdoors.

In at least some examples, the fluids within the electrowetting cell transmit at least 50% of the radiation in the preselected band after being exposed to an average illuminance of at least 80,000 lux for at least 1 hour. Because the illuminance may vary over time, the illuminance is the average illuminance over the stated time period. In other examples, the fluids transmit at least 50% of the radiation in the preselected band after being exposed to an average illuminance of at least 80,000 lux for at least 2 hours, for at least 4 hours, for at least 8 hours, for at least 16 hours, for at least 1 day, for at least 1 week, for at least 2 weeks, or for at least 3 weeks. In some examples, the fluids transmit at least 60% of the radiation in the preselected band after being exposed to an average illuminance of at least 80,000 lux for 1 hour, at least 75%, at least 80%, at least 85%, or at least 90% of the radiation in the preselected band.

In other examples, the fluids within the electrowetting cell transmit at least 50% of the radiation in the preselected band after being exposed to an average illuminance of 150,000 lux for 1 hour, at an average illuminance of 300,000 for 1 hour, at an average illuminance of 450,000 lux for 1 hour, at an average illuminance of 600,000 lux for 1 hour, at an average illuminance of 750,000 lux for 1 hour, at an average illuminance of 1,000,000 lux for 1 hour, at an average illuminance of 1,500,000 lux for 1 hour, at an average illuminance of 2,000,000 lux for 1 hour, or at an average illuminance of at least 2,500,000 lux for 1 hour.

As used herein, the term "preselected band" refers to a band of wavelengths that are predetermined for a particular use, such as, for example, an electrowetting cell for selectively, optically processing light output from a light source or an electrowetting cell for distributing radiation on a sensor. The preselected band may comprise a range, or band, of wavelengths within a given spectrum. For example, the preselected band may comprise a band of wavelengths within the visible spectrum. The preselected band need not be a continuous band, but may comprise multiple bands within a spectrum or spectrums.

In at least one example, the preselected band may comprise at least 5% of the wavelengths within the x-ray, ultraviolet, visible, infrared, microwave, or radiowave spectrums. For example, the visible spectrum comprises wavelengths in the range from 390 nm to 750 nm, a range of 360 nm. A preselected band comprises at least 5% of the wavelengths within the visible spectrum would have the required transmissivity over a range of at least 18 nm, such as the range from 400 nm to 418 nm or from 550 nm to 568 nm. Alternatively, a preselected band that comprises at least 5% of the wavelengths within the visible spectrum may comprise wavelengths in multiple bands, such as 400 nm to 409 nm and 610 nm to 619 nm. In a larger wavelength spectrum, such as the microwave spectrum, which comprises wavelengths ranging from 1 mm to 1 m, or a range of 99 mm, a preselected band comprising at least 10% of the wavelengths within the microwave spectrum would have the required transmissivity over a range of at least 9.9 mm, such as from 10 mm to 19.9 min.

In other examples, the preselected band may comprise at least 10% to 100% of the wavelengths within the x-ray, ultraviolet, visible, infrared, microwave, or radiowave spectrums. In one example, the conductive fluids may transmit at least 50% of the radiation over the entire visible spectrum, or at least 50% of the visible spectrum, i.e., a preselected band of 100% or at least 50% of the visible spectrum. Similarly, the preselected band may comprise at least 20%, at least 30%, at least 40%, at least 50%, at least 60%, at least 70%, at least 80%, or at least 90% of a given spectrum or spectrums. For example, the fluids may be capable of transmitting at least 50% of the radiation over at least 40% of the optical spectrum, which means that the fluids transmit at least 50% of the radiation over at least 40% of the wavelengths ranging from 10 nm to 1 mm.

According to at least some examples, the conductive fluid and non-conductive fluid should have densities within 10% of one another, such as, for example, within 7.5%, within 5%, or within 3%. Density may be measured in accordance with ASTM D-1217.

In at least one example, the surface tension of the conductive fluid is higher than the surface tension of the non-conductive fluid. For example, the conductive fluid may have a surface tension of greater than 50 mN/m, such as at least 55 mN/m, or at least 60 mN/m. The non-conductive fluid may have a surface tension less than 50 mN/m, such as less than 45 mN/m, less than 40 mN/m, or less than 38 mN/m. In at least one example, the surface tension of the conductive fluid differs from the surface tension of the non-conductive fluid by at least 10 mN/m, such as at least 15 mN/m, or at least 20 mN/m. The surface tension may be measured using a sessile drop test. The interfacial surface tension (IFT) of the fluid system can be calculated from taking contact angle measurements over a voltage range (e.g., with a First Ten Angstrom F121110 system) and fitting this to expected contact angles using the Young's Equation.

The first (non-conductive, e.g. insulating) fluid 111 may be a suitable oil. In some examples, the oil may include a silicon based fluid, such as, for example, a silane or a siloxane. In other examples, the oil may include a polyphenyl ether or polyphenylene oxide, in which the phenyl group is substituted with one or more alkyl groups, such as alkyl groups containing from 1 to 6 carbon atoms. The non-conductive fluid may also comprise a mixture of oils.

Some examples of a suitable silicon based fluids includes the compounds of Formula 1:

(Formula 1)

In Formula 1, $R^1$, $R^2$, and $R^3$ can be independently selected from H, a saturated or unsaturated, branched or linear C1 to C6 alkyl group, and a phenyl group. In at least one example, $R^1$, $R^2$, and $R^3$ are independently selected from methyl and phenyl groups.

R can be an aromatic group optionally substituted by one or more heteroatoms selected from N, O, and Si. In at least one example, R is an aromatic group selected from the group consisting of a benzotriazole, a pyrene, a phanthrene, a naphthenes, an anthracene, a benzofluorene, a benzofluoreneone, a fluoranthene, a diazobicyclo[2.2.1]hept-2-ene, and an indoquinoline In some examples, $R^1$ and R in Formula 1 are optionally linked to one another so as to define a ring.

In other examples, suitable silicon based fluids include compounds of Formula 2:

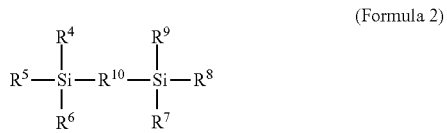

(Formula 2)

In Formula 2, $R^4$, $R^5$, $R^6$, $R^7$, $R^8$, and $R^9$ can be independently selected from H, a saturated or unsaturated, branched or linear C1 to C6 alkyl group, and a phenyl group. $R^{10}$ can be an aromatic group optionally substituted by one or more heteroatoms selected from N, O, and Si. In at least one example, $R^4$, $R^5$, $R^6$, $R^7$, $R^8$, and $R^9$ are independently selected from methyl or phenyl groups.

In yet other examples, the silicon based fluids can be selected from compounds of Formula 3:

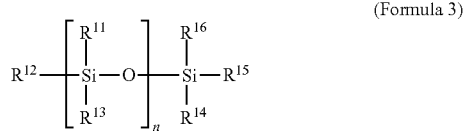
(Formula 3)

In Formula 3, $R^{11}$, $R^{12}$, $R^{13}$, $R^{14}$, $R^{15}$, and $R^{16}$ may be independently selected from H, a C1 to C6 alkyl group, and a phenyl group, and n is an integer from 1 to 5. When n is an integer from 2 to 5, each $R^{11}$ and $R^{13}$ group may be the same or different. For example, if n is 2, one $R^{11}$ group may be a phenyl group and the other $R^{11}$ group may be a methyl group. In at least one example, $R^{11}$, $R^{12}$, $R^{13}$, $R^{14}$, $R^{15}$, and $R^{16}$ are independently selected from methyl and phenyl groups. In some examples, the integer n is selected from 1 to 4, such that the compound of Formula 3 is a disiloxane, a trisiloxane, a tetrasiloxane, or a pentasiloxane.

According to at least some examples, the non-conductive fluid may have a flash point of at least 90° C., such as, for example, at least 95° C. or at least 100° C.

The refractive index of the non-conductive fluid may be at least 1.50 in some examples. In other examples, the refractive index of the non-conductive fluid may be at least 1.55 or at least 1.60.

Examples of the non-conductive fluid may include, but are not limited to, 1,1'-[bis(trimethylsilyl)methylen]bis(1H-benzotriazol), 1,6-pyrenediylbis(trimethylsilane), 5,5,7,7,12,12,14,14-octamethyl-5,7,12,14-tetrahydro[1]benzosilolo[3,2-b][1]benzosilolo[2',3':4,5]silolo[2,3-f][1]benzosilole, trimethyl(9-phenanthrylmethyl)silane, 2-[dimethyl(phenyl)silyl]-1-(1-naphthyl)-2,3-butadien-1-ol, 1,1,3,3-tetramethyl-1,3-dihydroanthra[2,3-c][1,2,5]oxadisilole, 4-methoxy-6-trimethylsilyl-4aH-benzo[c]fluoren-7-one, 1,1-dimethyl-1H-naphtho[1,8-bc]siline, 7-methyl-10-trimethylsilyl-10aH-benzo[h]fluoren-11-one, 4-methyl-6-trimethylsilyl-4aH-benzo[c]fluoren-7-one, [7,10-fluoranthenediylbis(1,1-ethenediyloxy)]bis(trimethylsilane), 6-methyl-10-trimethylsilyl-10aH-benzo[h]fluoren-11-one, 8-methoxy-10-trimethylsilyl-10aH-benzo[h]fluoren-11-one, 6-methoxy-10-trimethylsilyl-10aH-benzo[h]fluoren-11-one, 5-methyl-11-(trimethylsilyl)-5H-indolo[2,3-b]quinoline, 7,10-fluoranthenediylbis(trimethylsilane), 2,5-dimethyl-11-(trimethylsilyl)-5H-indolo[2,3-b]quinoline, trimethyl[(E)-2-(1,2,3,4-tetrahydro-1-anthracenyl)vinyl]silane, [9-anthryl(~2~H_1_)methyl](trimethyl)silane, (1R,4S)-7-[dimethyl(phenyl)silyl]-2,3-diazabicyclo[2.2.1]hept-2-ene, 8-methyl-10-trimethylsilyl-10aH-benzo[h]fluoren-11-one, 2-methyl-6-trimethylsilyl-4aH-benzo[c]fluoren-7-one, 2-methoxy-6-trimethylsilyl-4aH-benzo[c]fluoren-7-one, 7-methoxy-10-trimethylsilyl-10aH-benzo[h]fluoren-11-one, 1,1,3,3,4,4,6,6-octamethyl-1,3,4,6-tetrahydro[1,2,5]oxadisilolo[3',4':3,4]tetraceno[1,2-c][1,2,5]oxadisilole, 4,4,5,5-tetramethyl-4,5-dihydrophenanthro[4,5-cde][1,2]disiline, 3-methyl-6-trimethylsilyl-4aH-benzo[c]fluoren-7-one, [1,6-pyrenediylbis(methylene)]bis(trimethylsilane), 1-(trimethylsilyl)-5,6-dihydro[1,2,3]triazolo[5,1-a]isoquinoline, 1,1,5,5-tetraphenyl-1,3,3,5-tetramethyltrisiloxane, 3,5,7-triphenylnonamethylpentasiloxane, and 1,1,3,5,5-pentamethyl-1,3,5-trimethyltrisiloxane. In at least one example, the non-conductive fluid is 1,5,5-tetraphenyl-1,3,3,5-tetramethyltrisiloxane, 3,5,7-triphenylnonamethylpentasiloxane, or 1,1,3,5,5-pentamethyl-1,3,5-trimethyltrisiloxane.

The non-conductive fluid may contain an additive to adjust one or more of its properties, such as, the refractive index, surface tension, thermal stability, etc. In at least one example, the non-conductive fluid may contain a particulate. Particulates may range in size from nanoscale (e.g., 0.01 nm to 1 μm) to microscale (e.g., 1 μm to 1000 μm) or larger (e.g., greater than 1 mm). Examples of particulate additives include, but are not limited to, silicon dioxide, alumina, cobalt ferrite, carbon nanotubes, cerium oxides, titanium oxides, silver nanowires, or polymers, such as polymethyl methacrylate. In some examples, the particulates may be coated to further adjust attributes of the particles, such as, for example, suspension and motion properties or optical characteristics.

Suitable fluids for use as the second (conductive) fluid 112 include water, alcohols, glycols, ionic liquids, or other suitable liquid materials that can conduct electrical or ionic charges adequately to enable the electrowetting operations described herein. Conducting fluids may contain salts or other additives to alter their electrical conductivities, surface tension, temperature stability or optical properties. Specific examples of relatively conductive fluids that may be used include aqueous solutions for the more conductive liquid, such as: water, heavy water, glycols (propylene, ethylene, etc.), and mixtures thereof. The conductive fluid may contain an additive, such as, citric acid, sodium dodecyl sulfate (SDS), sodium lauryl sulfate (SLS), potassium chloride (KCl), Triton X-102, or boric acid and others. In at least one example, the conductive fluid comprises aqueous mixtures of sodium dodecyl sulfate (SDS), aqueous mixtures of potassium chloride (KCl), aqueous mixtures of citric acid, or propylene glycol (PG).

The fluid system, i.e., the combination of two fluids 111 and 112, should be stable over a wide operating range, such as, for example, from −20° C. to 100° C. For some applications, the lower operating temperature may extend down to 10° C., down to 0° C., down to −10° C., or down to −20° C. The upper limit of the operating temperature range may extend up to 100° C., up to 95° C., up to 90° C., up to 85° C., or up to 80° C. When the fluid system contains fluids with a boiling point higher than 100° C., the operating temperature can extend up to the boiling point of the lowest boiling temperature fluid in the system.

In the examples of shown FIGS. 1A-1C, both first and second plates and the associated end walls where radiation enters or exits can be transparent to the radiation. As a result, the electrowetting cell allows passage of radiation through the fluids within the cell, for example along and about the optical axis A-A. Radiation passing through such a cell may be refracted as a result of passage through the fluids in an amount dependent on the shape of the meniscus between the fluids, which is electrically controllable and refractive index difference between the fluids. Passage and such refraction of radiation through the cell may apply to radiation entering the cell in either direction, e.g. through either of the first and second plates and associated end walls. In such a cell, refracted radiation similarly may emerge from the cell in either direction, e.g. through either of the first and second plates and associated end walls.

A transmissive electrowetting cell bends or shapes radiation passing or transmitted through the electrowetting cell. The degree of bending or shaping varies with the angle or shape of the fluid interface surface in response to the applied electric field. Transmissive optics, for example, can take the form of a variable shaped lens, a variable shaped prism, combinations of prism and lens optics, or even a variable shaped grating formed by a wavefront across the interface surface.

Hence, the examples shown and described above in FIGS. 1A-1C relate to a transmissive electrowetting cell, that is to say a cell that acts as a lens and/or prism and is relatively transparent with respect to radiation that passes entirely through the optically active area of the cell. Teachings herein may also relate to reflective electrowetting cells. For a reflective cell, a reflector could either be at one end of the well (distal end or the first plate covering the opening of the well) or at the meniscus forming the interface of the two fluids. Alternatively, one of the fluids could be reflective, in which case that fluid itself could be used as reflector without adding any extra reflector.

A reflective electrowetting cell reflects radiation, and the angular redirection and/or shaping of the reflected radiation varies with the angle or shape of the fluid interface surface in response to the applied electric field. The two-liquid system may be controlled like a prism, e.g. in front of a mirror surface within the optic. Alternatively, the system may be configured such that the variable shaped surface itself is reflective.

FIGS. 3A to 3D are cross-sectional views of another example of a transmissive electrowetting type controllable optic 400, in several different states. The controllable electrowetting cell 400 in the example is controllable so as to provide variable prismatic properties to steer radiation as well as variable lens type properties to adjust focus and thus beam-shape of radiation passing through the optic 400. A controllable electrowetting cell 400 may be sized and coupled to a single or individual type of non-imaging radiation source. Alternatively, a number of a controllable electrowetting cells 400 may be sized and arranged in a multi-pixel array coupled to a non-imaging radiation source. The ray tracings are provided to generally illustrate the beam steering and beam shaping concepts in the different state examples and are not intended to indicate actual performance of the illustrated electrically controllable liquid prism-lens optic 400.

FIGS. 3A to 3D illustrate an example of controllable electrowetting cell 400 that includes an enclosed capsule 420 and voltage sources 425 and 426. The enclosed capsule 410 is configured to contain a non-conductive fluid, Liquid 1, and a conductive fluid, Liquid 2, as discussed above, that are responsive to an applied electric field based on voltages from the sources 425, 426. The drawings omit the hydrophobic surface(s), in the fluid system inside the capsule 420, for ease of illustration.

The liquids 1 and 2, for example, may be a silicon based fluid, as discussed above, and water (e.g., saline solution or an aqueous citric acid solution), respectively. The enclosed capsule 410, which in this example, has a physical shape of a cube or rectangular box, retains the liquids 1 and 2 to provide an electrically controllable liquid optic. Other electrowetting cell devices use enclosed capsules of different shapes.

The elements of the enclosed capsule 420 in the path of radiation flow through the optic 400 are formed of an appropriate transparent material, such as glass, plastic or silicone. In the transmissive prism-lens example, radiation enters one transmissive wall of the capsule 420, passes through the liquids and exits the optic from another transmissive wall of the capsule 420. As will be discussed more later, one form of a reflective electrowetting cell replaces or coats the second transmissive wall of the capsule 420 with a suitable reflective material. Any electrodes or leads providing connections to the electrodes formed in the optical path 400 are formed of an optically transmissive electrical conductor. Any electrode or connections not in the optical path need not be transparent and therefore may be formed of any metal or other suitable conductor.

In the example of FIGS. 3A to 3D, the enclosed capsule 420 includes terminals 427A and 427B that couple to voltage source 425C as well as terminals 427C and 427D that couple to voltage source 426. The terminals 427A and 427B are further coupled to electrodes 1 and 2, and terminals 427C and 427D are further coupled to electrodes 3 and 4. The liquids 1 and 2 respond to voltages applied to the electrodes 1-4 to provide a combination of beam steering and beam shaping functions, in this prism-lens type combined electrowetting cell. The substrate in contact with the conductive liquid (e.g., water) will always be connected to ground. For convenience, the ground electrode is not shown in FIGS. 3A to 3D.

The shape of the interface surface between liquids 1 and 2 and thus the optical functionality of the optic 400 may be manipulated by adjusting the voltages applied by voltage sources 425 and 426. For example, the voltages V1 and V2 may not be equal. The voltages V1 and V2 may be applied simultaneously at different values to achieve a particular state. Although the voltages V1 and V2 are described as being applied simultaneously, the voltages V1 and V2 may be applied separately. Different values and timing of applied voltages produce different electric fields resulting in different shapes of the surface at the interface between the two liquids.

The controllable electrowetting cell 400 responds to the variable electric field created by applying different voltages from voltage sources 425 and 426 to attain the different states 1-4 illustrated by the four different examples. The states 1 and 3 provide different angular beam steering but with similar focusing beam shaping, while states 2 and 4 provide different angular beam steering but with similar defocusing beam shaping. The voltage sources 425 and 426 may apply voltages of different values including different polarities that enable the electrowetting cell 400 to provide variations of states 1-4 that may be used to process radiation according to different spatial modulation selections, to provide different shape and angular aspects of the output distribution of a software configurable lighting device 11. Although four states are shown, different variations of the voltages can cause the electrowetting cell to place the fluids in a variety of other states, with other shapes for the interface surface between the two liquids.

Figure 4A:
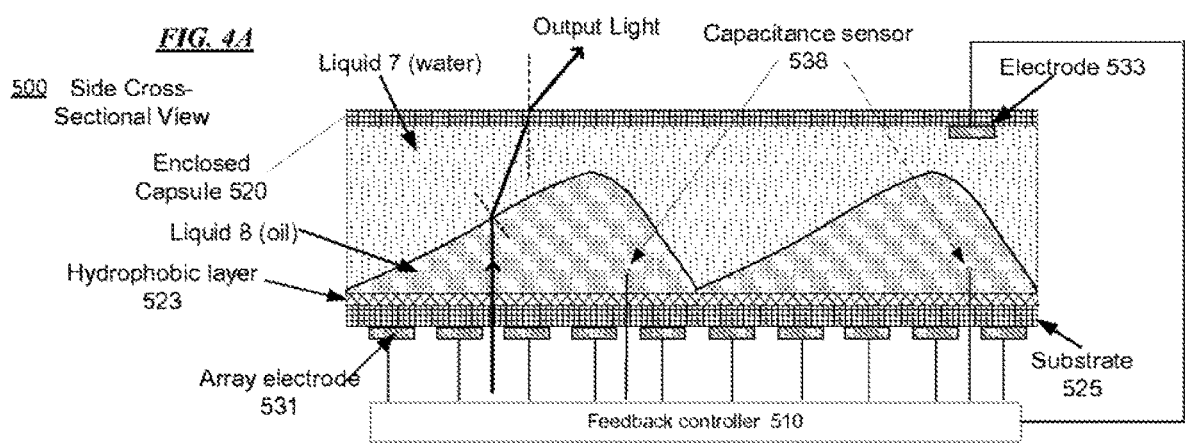
FIGS. 4A and 4B are different cross sectional views of an example of another type of an electrowetting cell that provides waveform control at the liquid interface, to provide selectable beam steering and/or beam shaping.
Figure 4B:
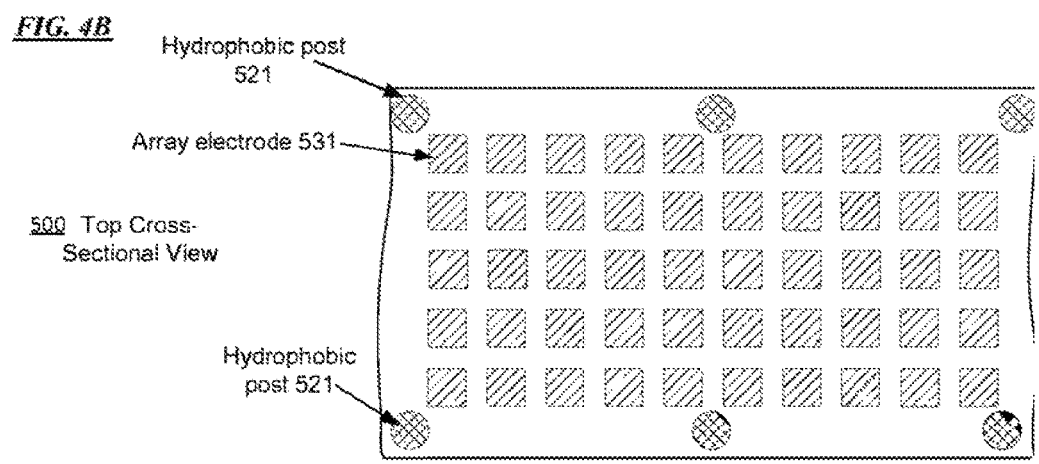

Another example of a controllable electrowetting cell 500 is shown in FIGS. 4A and 4B. The electrowetting cell 500 illustrated in FIGS. 4A and 4B is able to provide a standing wave or a moving wave configuration of the interface surface between two liquids, as illustrated in FIG. 4A. The waveform of the surface provides different degrees of refraction across the optic, for shaping and steering radiation passing through the optic at different locations. The waveform is produced by electric fields, and variation of the fields changes the waveform shape and thus the spatial modulation produced to different degrees across the optic 500.

The electrowetting cell 500 includes an enclosed capsule 520, which contains a liquid 7 (e.g., water) and a liquid 8 (e.g., a silicon based fluid), similar to the liquids discussed with regard to the earlier electrowetting examples. The enclosed capsule 520 has or includes a wall that forms a substrate 525. Elements of the capsule 520 forming walls that are in the path of radiation passing through the optic 500, such as the substrate 520 are transparent. A reflective wall or a reflector at the interface surface may be provided to adapt the optic 500 to a reflective beam steering application, although further discussion of the example of FIGS. 4A and 4B will concentrate mainly on the illustrated transmissive implementation.

The enclosed capsule 520, also contains a hydrophobic dielectric layer 523, which also is transparent. The hydrophobic dielectric layer 523 provides a surface that repels liquids. This hydrophobic layer can be created by conformal deposition of a dielectric layer or a combination of dielectric layers using materials such as parylene, fluoropolymers, etc. These dielectric layers control the No-voltage contact angle of the liquids, and also to an extent the voltage response of the electrowetting device especially the breakdown voltage. A hydrophobic dielectric post 521 is a support member as shown in FIG. 3B, but is not shown in FIG. 3A for ease of illustration. The hydrophobic post 521 in some examples, is used to establish an initial flat film of the liquid 8 (e.g. silicon based fluid) in the absence of a voltage from feedback controller 510.

The enclosed capsule 520 also includes one or more capacitance sensors 538. The capacitance sensors 538 are responsive to capacitances between the liquid water and electrodes of the array 531 and connected to provide feedback to the controller 510.

The enclosed capsule 520 also includes an array of electrodes 531 and electrode 533. The array of electrodes 531 and possibly the electrode 533 may be transparent. The array electrodes 531 and the electrode 533 are coupled to a feedback controller 510. Voltages applied to the electrodes of the array 531 (relative to the electrode 533) are individually controllable by the feedback controller 510 in response to a control signal provided by a higher level logical control element such as the microprocessor of a host processor system (not shown). The feedback controller 510 in response to signals from the capacitance sensors 538 manipulates the voltages applied to the array electrodes 531 to maintain a desired standing or moving wave in liquids 7 and 8.

In an example, an initial high voltage is applied by the feedback controller 510 at a specific electrode in the array electrodes 531 to dewet the liquid 8 (silicon based fluid) so that the oil begins to rise away from the hydrophobic layer 523. However, before the oil completely dewets the hydrophobic dielectric layer 523, which is determined based on the capacitance between the water and electrode according to measurements by the capacitance sensor 538, the voltages applied to the array of electrodes 531 are switched back to a lower voltage to undewet the hydrophobic dielectric surface 523. This process is performed over multiple instances such that the thickness of liquid 8 (silicon based fluid) at that particular electrode in the array of electrodes 531 will reach a substantially stable thickness at a particular electrode of the array of electrodes 531. As a result, a standing wave lens and/or prism structure may be achieved. In another example, a moving wave structure may be achieved by dynamically controlling the voltage to the patterned electrodes of the array of electrodes 531.

It should be noted that the geometry of the oil/water interface surface is not limited to prism shapes like that shown in FIG. 4A. The lens or prism geometries provided by waveform selection could be any combination of vertically oriented convex and concave oil geometries as long as there are adequate electrodes, the aspect ratio is not too great, and control signals provided to the feedback controller 510 provide the selected waveform for a desired optical spatial modulation.

It is also envisioned that prism or lens geometries may be created that will move horizontally (e.g., left to right through the enclosed capsule 520) with time. For example, voltages at a particular frequency and timing may be applied to individual electrodes of the array electrodes 531 to generate standing waves in a time sequence, such that the standing waves appear as a constant geometry.

FIG. 4B illustrates a top-down cross-sectional view of the electrowetting cell 500 in the example of FIG. 4A. The electrowetting cell 500, as did the similar electrowetting prism-lens in the earlier example, includes transparent surfaces and electrodes that do not add significant optical processing (e.g., refraction) to the radiation output from the optic. As a result, the number of array electrodes 531 in electrowetting cell 500 under control of the feedback controller 510, or a processor, such as microprocessor 123 of host processor 115, may provide complex wavefronts in various locations across the optic to provide the selected spatial modulation.

The controllable electrowetting cell 500 may be sized and coupled to any of a number of radiation sources (e.g. light sources) to operate as an individual pixelated spatial modulator.

As shown by the examples of FIGS. 3A-4B, electrowetting cells are a useful technology for implementing controllable beam steering and/or beam shaping for software configurable lighting devices. However, for lighting devices, there may be a need for relatively large beam steering angles. In a two-fluid electrowetting cell, the optical path is related to the refractive indices of liquids that are used. To achieve the maximum deflection angle, fluids having a greater difference in refractive index must be used. In addition, a large beam steering angle requires large contact angle between the non-conductive and conductive fluids, which requires higher operating voltage.

Figure 5:
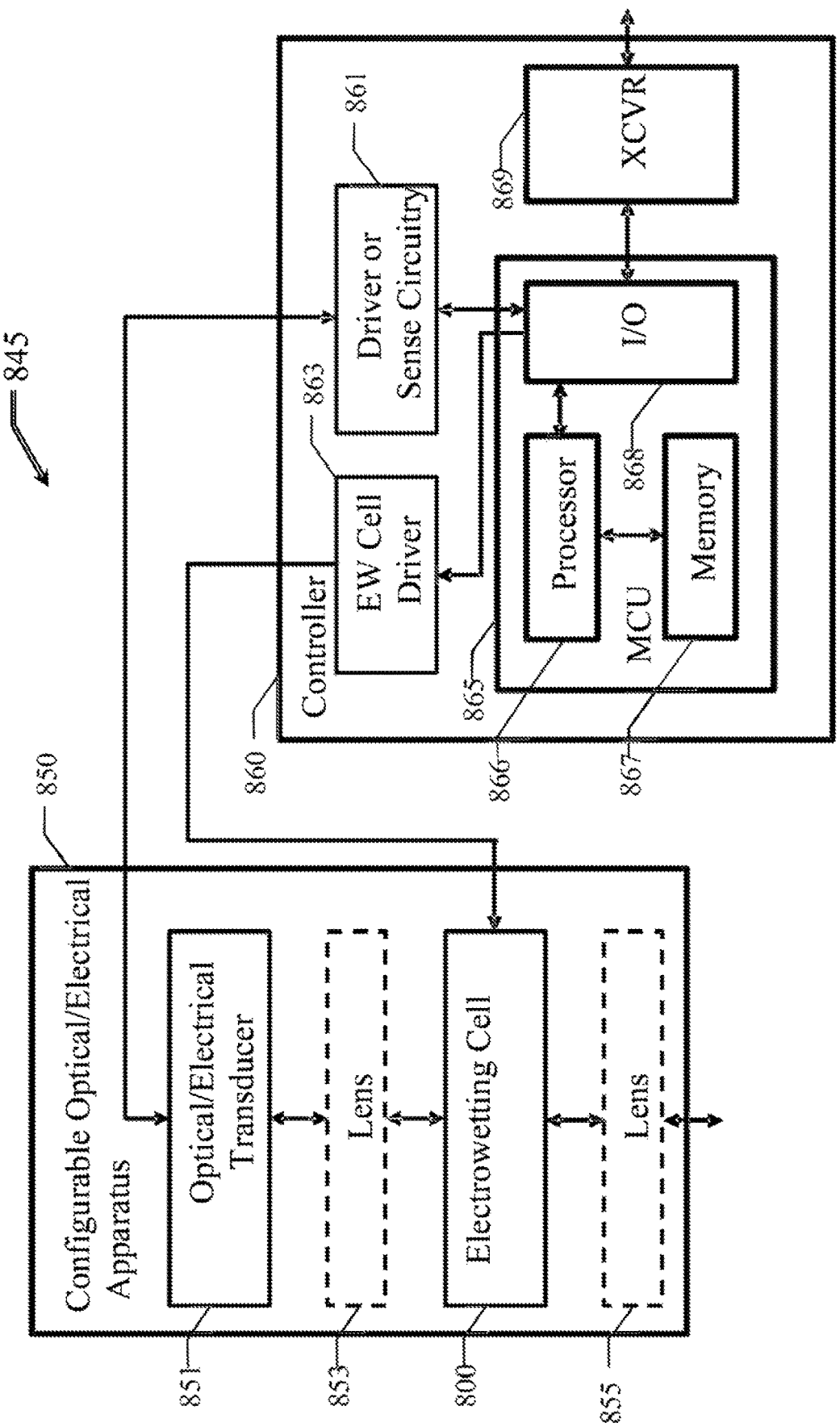
FIG. 5 is a simplified functional block diagram of a system combining an electrowetting cell like that described with an optical/electrical transducer and associated circuitry.

FIG. 5 is a simplified functional block diagram of a system 845, which includes a configurable optical/electrical apparatus 850 and a controller 860. The configurable optical/electrical apparatus 850 combines an electrowetting cell like that described above in FIGS. 1A-1C with an optical/electrical transducer 851. Although associated circuitry may be provided in the apparatus 850, the example shows circuitry in the controller 860, which may be somewhat separate from or even remote from the configurable optical/electrical apparatus 850.

An optical/electrical transducer 851 is a device that converts between forms of optical and electrical energy, for example, from optical energy to an electrical signal or from electrical energy to an optical output. Examples of optical-to-electrical transducers include various sensors or detectors, photovoltaic devices and the like. Optical-to-electrical transducers discussed herein are responsive to radiation, and the radiation may be visible light, ultraviolet light, infrared, near infrared or light in other portions of the optical spectrum.

Examples of electrical-to-optical transducers include various light emitters, although the emitted light may be in the visible spectrum or in other wavelength ranges. Suitable light generation sources for use as the transducer 851 include various conventional lamps, such as incandescent, fluorescent or halide lamps; one or more light emitting diodes (LEDs) of various types, such as planar LEDs, micro LEDs, micro organic LEDs, LEDs on gallium nitride (GaN) substrates, micro nanowire or nanorod LEDs, photo pumped quantum dot (QD) LEDs, micro plasmonic LED, micro resonant-cavity (RC) LEDs, and micro photonic crystal LEDs; as well as other sources such as micro super luminescent Diodes (SLD) and micro laser diodes. Of course, these light generation technologies are given by way of non-limiting examples, and other light generation technologies may be used to implement the transducer 851. For example, it should be understood that non-micro versions of the foregoing light generation sources can be used.

When optical transducer 851 is a light source, the light source may use a single emitter to generate light or may combine light from some number of emitters that generate the light. A lamp or 'light bulb' is an example of a single source. An LED light engine may use a single output for a single source but typically combines light from multiple LED type emitters within the single light engine. Many types of light sources provide an illumination light output that generally appears uniform to an observer, although there may be some color or intensity striations, e.g. along an edge of a combined light output. For purposes of the present examples, however, the appearance of the light source output may not be strictly uniform across the output area or aperture of the source. For example, although the source may use individual emitters or groups of individual emitters to produce the light generated by the overall source; depending on the arrangement of the emitters and any associated mixer or diffuser, the light output may be relatively uniform across the aperture or may appear pixelated to an observer viewing the output aperture. The individual emitters or groups of emitters may be separately controllable, for example to control intensity or color characteristics of the source output. As such, the light source used as an emitter type of optical/electrical transducer 851 may or may not be pixelated for control purposes. The electrowetting cell 800 is controlled to selectively optically change or spatially (optically) modulate the light distribution output from the transducer and thus from the apparatus 850. The electrowetting cell 800 may support controlled beam steering, controlled beam shaping or a combination of controlled beam steering and shaping.

In another example, optical transducer 851 is an optical-to-electrical converter, that is to say, a light sensor or detector or a photovoltaic device. The overall apparatus 850 in such a case may be configured as an imager, other light responsive sensor, light responsive power source, or the like. The light detector may be an array of light detectors, a photo-detector such as a photodiode, or a photovoltaic device, depending on the desired function of optical/electrical apparatus 850. Other suitable light detectors for use as optical/electrical transducer 851 include charge-coupled device (CCD) arrays, complementary metal-oxide-semiconductor (CMOS) arrays, photomultipliers, image intensifiers, phototransistors, photo resistors, thermal imagers, and micro-electromechanical systems (MEMS) imagers. Nonetheless, virtually any detector of light may be used as the transducer 851 in an optical-to-electrical arrangement of apparatus 860. Suitable light detectors will be known to one of ordinary skill in the art from the description herein. The electrowetting cell 800 is controlled to selectively optically change or spatially (optically) modulate the field of view of light coming into the apparatus 850 for delivery to transducer 851. The electrowetting cell 800 may support controlled beam steering, controlled beam shaping or a combination of controlled beam steering and shaping, with respect to light from a field of intended view for the particular optical-to-electrical application of the apparatus 850.

While light source examples and light detector examples are described separately, it will be understood that both types of optical/electrical transducers 851 may be present in a single optical apparatus 850 and/or some optical transducers can serve both input and output functions (e.g. some LEDs can be multiplexed between the emitting operation and a light detection operation). Such a combined arrangement or operation, for example, may advantageously provide capabilities to reconfigure the light output distribution in accordance with a desired light detection pattern.

In an overall apparatus 850, with an optical/electrical transducer 851, the electrowetting cell 800 may have a lens on one side or the other side or have lenses on both sides, of the electrowetting cell 800, along the axis of the optical path through the cell 800 and to or from the transducer 851. Hence, FIG. 5 shows a dotted line (optional) example of a lens 853 between the transducer 851 and the electrowetting cell 800. Similarly, FIG. 5 shows a dotted line (optional) example of a lens 855 on the side of the electrowetting cell 800 opposite the transducer 851. In the example, the lenses 851 or 853 would be fixed lenses.

Various examples of arrangements of a spatial optical modulator (e.g. as an electrowetting cell) with one or more cascaded lenses are disclosed in U.S. patent application Ser. No. 15/228,414, filed Aug. 4, 2016, entitled "Configurable Optical Transducers Using An Optical Modulator And One Or More Lenses," the disclosure of which is entirely incorporated by reference.

Although not shown, additional optical processing elements may be provided in the apparatus 850. In a luminaire for general illumination or in another type of light emission device (e.g. a flash), an emitter type transducer 851 may be coupled to the electrowetting lens 100 via a collimating optic, such as a total internal reflection (TIR) lens.

A transducer 851, such as a light emitter or a light detector, often connects to corresponding electrical circuitry to operate the particular type of transducer, e.g. a driver circuit to supply power to an emitter or a sense circuit to process an output signal from a detector (and provide power to the detector if necessary). Hence, to operate the transducer 851, the controller 860 includes corresponding driver or sense circuitry 861. The type of circuitry 861 would depend on the type of transducer 851.

The controller 860 includes an electrowetting (EW) driver 863 to selectively provide signals to the electrodes (e.g. voltages between respective control channel electrodes and the common electrode) to control the fluid state of the electrowetting cell 800. The driver 863, for example, may be circuitry constructed/configured to apply direct current (DC) voltages or alternating current (AC) voltages or AC with a DC offset to the cell electrodes. In the example 800 of the cell above, having four control channel electrodes and a common electrode, the EW driver 863 would have four separately controllable voltage output channels each having a connection through a respective contact to a respective one of the control channel electrodes. Each separately controllable voltage output channel of the EW driver 863 would also have a connection through the common contact to the common electrode of the electrowetting cell 800. Configuration of the circuitry of the EW driver 863 would be adapted to the particular electrical control strategy (e.g. to use AC, DC or a combination of AC and DC), the intended range(s) of fluid states and thus to the beam steering and/or shaping capabilities of the electrowetting cell 800, and/or to any voltage or current limitations intended to minimize damage to the cell structure of components thereof during operation of the system 845.

The controller 860 also includes a processor, one or more digital storage media, data and programming in the storage and appropriate input/output circuitry. Although other processor based architectures may be used (another example is described later regarding FIG.), the example of controller 860 utilizes a Micro-Control Unit (MCU) 865, which implements the control logic for the controller 860 and thus of the system 845. For example, the MCU 865 implements the logic for control of operations of the associated optical/electrical apparatus 850. Although shown as controlling only one such apparatus 850, the MCU and controller may control a number of such apparatuses 850.

The MCU 865 may be a microchip device that incorporates a processor 866 serving as the programmable central processing unit (CPU) of the MCU 865 as well as one or more memories, represented by memory 867 in the drawing. The memory 867 is accessible to the processor 866, and the memory or memories 867 store executable programming for the CPU formed by processor 866 as well as data for processing by or resulting from processing of the processor 866. The MCU 865 may be thought of as a small computer or computer like device formed on a single chip. Such devices are often used as the configurable control elements embedded in special purpose devices rather than in a computer or other general purpose device. A variety of available MCU chips, for example, may be used as the MCU 865 in the controller 860 of system 845.

The MCU 865 in this example also includes various input and output (I/O) interfaces, shown collectively by way of example as interface 868 in FIG. 5. The I/O interfaces 868, for example, support a control output to the EW cell driver 863 as well as a control output and/or input to the driver or sense control circuitry 861 (for the optical/electrical transducer 851). The I/O interfaces 868 also support input/output communications with one or more electronic devices, which may be connected to or incorporated in the system 845 (e.g. to provide a user interface not shown) or which may be remote.

In the illustrated example, the controller 860 also includes a communication transceiver (XCVR) 869 coupled to the processor 166 (and possibly to the memory 867) via an I/O output interface 868 of the MCU 865. Although shown separately, the transceiver 869 may be implemented in circuity on the same chip as the elements of the MCU 865. Although the drawing shows only one transceiver 869, controller 860 may include any number of transceivers, for example, to support additional communication protocols and/or provide communication over different communication media or channels.

The transceiver 869 supports communication with other control or processing equipment, for example, with a remote user interface device and/or with a host computer of a building control and automation system (BCAS). The transceiver 869 may also support system communication with a variety of other equipment of other parties having access to the system 845 in an overall/networked system encompassing a number of similar systems 845, e.g. for access to each system 845 by equipment of a manufacturer for maintenance or access to an on-line server for downloading of programming instructions or configuration data for setting aspects of sensing or lighting operation of the associated optical/electrical apparatus(s) 850. The circuitry of the transceiver 869 may support such communication(s) over any available medium, such as wire(s), cable, optical fiber, free-space optical link or radio frequency (RF) link.

Although the examples shown in FIGS. 1, 2, 3, and 5 include a single electrowetting cell, multiple cells can be used within a single device. In examples using multiple electrowetting cells, the cells may be arranged in arrays. Various examples of arrangements of a controllable electrowetting array with one or more cascaded lenses are disclosed in U.S. patent application Ser. No. 15/389,829, filed Dec. 23, 2016, entitled "Electrowetting Cellular Array And Luminaire Incorporating The Array," U.S. patent application Ser. No. 15/234,031, filed Aug. 11, 2016, entitled, "Configurable Lighting Device Using A Light Source And Optical Modulator," and U.S. patent application Ser. No. 15/209,878, filed Jul. 14, 2016, entitled "Software Configurable Lighting Device," the disclosures of which are entirely incorporated by reference.

The processor 866 of the MCU 865 (FIG. 5) is an example of a processor that may be used to control an electrowetting cell or array of such cell and control or respond to outputs of any associated optical/electrical transducer(s). As used herein, a processor is a hardware circuit having elements structured and arranged to perform one or more processing functions, typically various data processing functions. Although discrete logic components could be used, the examples utilize components forming a programmable central processing unit (CPU). A processor for example includes or is part of one or more integrated circuit (IC) chips incorporating the electronic elements to perform the functions of the CPU.

The processor 866 executes programming or instructions to configure the system 845 to perform various operations. For example, such operations may include various general operations (e.g., a clock function, recording and logging operational status and/or failure information) as well as various system-specific operations (e.g. controlling beam steering and beam shaping of input or output light, operation of the transducer(s) and the like) of an optical/electrical apparatus 860 incorporating one or more of the electrowetting cells and associated transducer(s). Although a processor may be configured by use of hardwired logic, typical processors in lighting devices are general processing circuits configured by execution of programming, e.g. instructions and any associated setting data from the memories shown or from other included storage media and/or received from remote storage media.

As outlined above, a class of applications of the cell 800 with suitable light source type transducers provide configurable luminaires. The term "luminaire," as used herein, is intended to encompass essentially any type of device that processes energy to generate or supply artificial light, for example, for general illumination of a space intended for use of occupancy or observation, typically by a living organism that can take advantage of or be affected in some desired manner by the light emitted from the device. However, a luminaire may provide light for use by automated equipment, such as sensors/monitors, robots, etc. that may occupy or observe the illuminated space, instead of or in addition to light provided for an organism. However, it is also possible that one or more luminaires in or on a particular premises have other lighting purposes, such as signage for an entrance or to indicate an exit. In most examples, the luminaire(s) illuminate a space or area of a premises to a level useful for a human in or passing through the space, e.g. general illumination of a room or corridor in a building or of an outdoor space such as a street, sidewalk, parking lot or performance venue. The actual source of illumination light in or supplying the light for a luminaire may be any type of artificial light emitting device, several examples of which are included in the discussions below. Other large format lighting applications for the electrowetting cell constructs include vehicle lighting or the like.

Terms such as "artificial lighting," as used herein, are intended to encompass essentially any type of lighting that a device produces light by processing of electrical power to generate the light. An artificial lighting device, for example, may take the form of a lamp, light fixture, or other luminaire that incorporates a light source, where the light source by itself contains no intelligence or communication capability, such as one or more LEDs or the like, or a lamp (e.g. "regular light bulbs") of any suitable type. The illumination light output of an artificial illumination type luminaire, for example, may have an intensity and/or other characteristic(s) that satisfy an industry acceptable performance standard for a general lighting application.

Artificial light output from a luminaire may carry information, such as a code (e.g. to identify the luminaire or its location) or downstream transmission of communication signaling and/or user data. The light based data transmission may involve modulation or otherwise adjusting parameters (e.g. intensity, color characteristic or optical spatial distribution) of the illumination light output from the device.

Another class of applications for the electrowetting cell relate to sensing applications. A sensing application typically combines a detector type transducer with one or more electrowetting. The detector, for example, may be a single light responsive component, a combination of several light responsive components detecting the same or different light characteristics, or a pixel array of light detectors (e.g. for image sensing). Although some photovoltaic devices may output power in response to optical energy, sensors typically involve some processing circuitry to operate the particular type of detector.

Displays and a variety of other applications of the electrowetting cell also are within the scope of the disclosure above.

EXAMPLES

During testing of electrowetting cells with two-fluid systems, we observed that some fluids used became cloudy or discolored (e.g., yellowed) with prolonged application of light and heat. This haziness or discoloration adversely affects the amount of light transmitted through the electrowetting cell. With many conventional fluid systems, the haziness or discoloration occurs rapidly and can be observed in as little as 15-35 minutes. With further application of light and heat, some devices developed a thin film at the interface for the fluids.

We conducted testing to determine the cause of the cloudiness and discoloration to identify new fluid systems for use in electrowetting cells. Additionally, we investigated whether the use of additives made any sort of improvement.

Applicable Tests Performed:

Example 1: Illumination Only of Individual Fluids

Each fluid was separated into small quantities in sealed glass containers and illuminated with a LED with the expected intensity and spectrum that the final device would encounter. This test provided a control to determine whether clouding or discoloration of individual fluids occurred by illumination alone. The results shown in Table 1 demonstrate that luminous flux alone did not affect the appearance of the individual components.

TABLE 1

| Fluid | Time of Clouding/Yellowing |
|---|---|
| 1-Methylnaphthalene | Never observed |
| 1-Phenylnaphthalene | Never observed |
| Distilled water | Never observed |
| 0.1 wt % Citric Acid in Distilled water | Never observed |

Example 2: Heat Only of Individual Fluids

Each fluid was separated into small quantities in sealed glass containers and subjected to heat in an oven at specific temperature steps for a given length of time (4 hr minimum) to determine whether individual fluids were affected by heat alone. The results shown in Table 2 show that heating in an oven did not affect the individual components.

TABLE 2

| Fluid | Temperature (° C.) | Time of Clouding/Yellowing |
|---|---|---|
| 1-Methylnaphthalene | 25-85 | Never observed |
| 1-Phenylnaphthalene | 25-85 | Never observed |
| Distilled water | 25-85 | Never observed |
| 0.1 wt % Citric Acid in Distilled water | 25-85 | Never observed |

Example 3: Directional Heat Only of Individual Fluids

Each fluid was separated into small quantities in sealed glass containers and placed onto a hotplate at the maximum expected operating temperature of the final device. This test provided a control to determine whether directional heat would cause haziness or discoloration of individual fluids. As shown in Table 3, clouding/yellowing was observed in 1-methylnaphthalene and 1-phenylnaphthalene after 4 or 3 hours, respectively, of exposure to directional heating at 75° C.

TABLE 3

| Fluid | Temperature (° C.) | Time of Clouding/Yellowing |
|---|---|---|
| 1-Methylnaphthalene | 75 | 4 hours |
| 1-Phenylnaphthalene | 75 | 3 hours |
| Distilled water | 75 | Never observed |
| 0.1 wt % Citric Acid in Distilled water | 75 | Never observed |

Example 4: Directional Heat Only of Select Immiscible Fluid Pairs

Each fluid pair was sealed within test devices with expected operational fluid volumes. Each device was placed onto a hotplate at the maximum expected operating temperature of the final device. The results shown in Table 4 show that most of the fluid systems using conventional non-conductive fluids exhibit clouding or yellowing within an hour of exposure to direct heat. Non-conductive fluids according to the examples discussed above demonstrated much greater resistance to clouding or yellowing.

TABLE 4

| Fluid | Temperature (° C.) | Time of Clouding/Yellowing |
|---|---|---|
| 1-Methylnaphthalene + 0.1 wt % Citric Acid in Distilled water | 75 | Clouding of 1-Methylnaphthalene only: 45-60 minutes, no yellowing |

TABLE 4-continued

| Fluid | Temperature (° C.) | Time of Clouding/ Yellowing |
|---|---|---|
| 1-Phenylnaphthalene + 0.1 wt % Citric Acid in Distilled water | 75 | Clouding of 1-Phenylnaphthalene only: 40-60 minutes, no yellowing |
| 1-Methylnaphthalene + 1 wt % Citric Acid in Distilled water | 75 | Clouding of 1-Methylnaphthalene only: 40-60 minutes, no yellowing |
| 1-Phenylnaphthalene + 1 wt % Citric Acid in Distilled water | 75 | Clouding of 1-Phenylnaphthalene only: 30-45 minutes, no yellowing |
| 1-Methylnaphthalene + 1 wt % Ammonium Sulfate in Distilled water | 75 | Clouding of 1-Methylnaphthalene only: 60 minutes, no yellowing |
| 1-Methylnaphthalene + 1 wt % Zinc Sulfate in Distilled water | 75 | Clouding of both phases: 60 minutes, no yellowing |
| 1-Methylnaphthalene + 1 wt % Magnesium Sulfate in Distilled water | 75 | Clouding of 1-Methylnaphthalene only: 60 minutes, no yellowing |
| 1-Methylnaphthalene + 5 wt % Glucose in Distilled water | 75 | Clouding of both phases: 60 minutes, no yellowing |
| 1-Methylnaphthalene + 5 wt % Urea in Distilled water | 75 | Clouding of 1-Methylnaphthalene only: 60 minutes, no yellowing |
| 1-Methylnaphthalene + 20 wt % Urea in Distilled water | 75 | Clouding of 1-Methylnaphthalene only: 60 minutes, no yellowing |
| 1-Methylnaphthalene + 50 wt % Ethylene Glycol in Distilled water | 75 | Clouding of both phases: 60 minutes, no yellowing |
| 1-Methylnaphthalene + 50 wt % Propylene Glycol in Distilled water | 75 | Clouding of both phases: 60 minutes, no yellowing |
| 1-Methylnaphthalene + 50 wt % Glycerol in Distilled water | 75 | Clouding of both phases: 60 minutes, no yellowing |
| 1-Methylnaphthalene + 50 wt % Glycerol Carbonate in Distilled water | 75 | Clouding of both phases: 60 minutes, no yellowing |
| 1-Methylnaphthalene + 2:1 Urea:Choline Chloride/Methyl Oleate in Distilled water | 75 | No clouding observed |
| 1-Methylnaphthalene + 40 wt % Urea in Distilled water | 75 | Clouding of 1-Methylnaphthalene only: 60 minutes, no yellowing |
| 1-Methylnaphthalene + Ethylene Glycol | 75 | Clouding of both phases: 60 minutes, no yellowing |
| 1-Methylnaphthalene + Propylene Glycol | 75 | Clouding of both phases: 60 minutes, no yellowing |
| 1,1,5,5-Tetraphenyl-1,3,3,5-Tetramethyltrisiloxane + 0.1 wt % Citric Acid in Distilled Water | 75 | No clouding/yellowing after 17 hours. Clouding when heat removed |
| 3,5,7-Triphenylnonamethylpentasiloxane + 0.1 wt % Citric Acid in Distilled Water | 75 | No clouding/yellowing after 17 hours. Clouding when heat removed |
| 50 wt % 1,1,5,5-Tetraphenyl-1,3,3,5-Tetramethyltrisiloxane in 1-Methylnaphthalene + 0.1 wt % Citric Acid in Distilled Water | 75 | No clouding/yellowing after 17 hours. Clouding when heat removed |

Example 5: Illumination of Finalized Devices with LED Source and No Heat Decoupling Select fluid pairs were sealed within test devices with expected operational fluid volumes. Each device was placed onto a LED light source with no heat decoupling. Table 5 shows that clouding and yellowing of the conventional fluids occurred. The silicon based fluids, according to the examples discussed above, were not observed to discolor or cloud.

TABLE 5

| Fluid | Temperature (° C.) | Time of Clouding/ Yellowing |
|---|---|---|
| 1-Methylnaphthalene + 0.1 wt % Citric Acid in Distilled water | 75 | Clouding: 15-30 minutes; Yellowing: 60 minutes; occasionally semi-solid film within 24 hours |
| 1-Phenylnaphthalene + 0.1 wt % Citric Acid in Distilled water | 75 | Clouding: 15-20 minutes; semi-solid film formed within 8 hours |
| 1,1,5,5-Tetraphenyl-1,3,3,5-Tetramethyltrisiloxane + 0.1 wt % Citric Acid in Distilled water | 75 | Film formed at fluid interface after 14 days |
| 1,1,5,5-Tetraphenyl-1,3,3,5-Tetramethyltrisiloxane + Distilled water | 75 | Film formed at fluid interface after 14 days |
| Santolight ™ SL-5267 + 0.1 wt % Citric Acid in Distilled water | 75 | Clouding and yellowing: less than 24 hours; Santolight ™ SL-5267 solidification occurred |

Example 6: Illumination of Finalized Devices with Controlled Ambient Temperature Select fluid pairs were sealed within test devices with expected operational fluid volumes. Each device was placed onto a light coupling stand of varied heights to decouple the heat of the LED from the device. The luminance flux of the LED ranged from 130 to 160 lumens and the device had a circular aperture of approximately 16 mm in diameter, thus providing an illuminance of about 646,000 to about 795,000 lux. Gelest PDM-7050 comprises 1,1,3,5,5-pentamethyl-1,3,5-trimethyltrisiloxane. The results shown in Table 6 demonstrate that fluid systems using Gelest PDM-7050 do not yellow or cloud for more than 2 weeks in this test.

TABLE 6

| Fluid | Temperature (° C.) | Time of Clouding/ Yellowing |
|---|---|---|
| Gelest PDM-7050 + 0.1 wt % Citric Acid in Distilled water | 27 | No clouding observed after 28 days |
| Gelest PDM-7050 + Distilled water | 27 | Clouding only observed after 17 days |
| 1-Methylnaphthalene + 0.1 wt % Citric Acid in Distilled water | 27-32 | Clouding and yellowing within 24 hours |
| 1-Phenylnaphthalene + 0.1 wt % Citric Acid in Distilled water | 27-32 | Clouding and yellowing within 24 hours |
| 1-Methylnaphthalene + 1 wt % Citric Acid in Distilled water | 27-32 | Clouding and yellowing within 24 hours |
| 1-Phenylnaphthalene + 1 wt % Citric Acid in Distilled water | 27-32 | Clouding and yellowing within 24 hours |
| SL-6257 + 1 wt % Citric Acid in Distilled water | 27-32 | Yellowed/browned and partially solidified within 72 hours |
| SL-6257 + Distilled water | 27-32 | Yellowed/browned and partially solidified within 72 hours |
| 50 wt % 1,1,5-Tetraphenyl-1,3,3,5-Tetramethyltrisiloxane in 1-Methylnaphthalene + 0.1 wt % Citric Acid in Distilled Water | 32-35 | Yellowed within 24 hours. |

TABLE 6-continued

| Fluid | Temperature (° C.) | Time of Clouding/Yellowing |
|---|---|---|
| 50 wt % 1,1,5,5-Tetraphenyl-1,3,3,5-Tetramethyltrisiloxane in 1-Phenylnaphthalene + 0.1 wt % Citric Acid in Distilled Water | 32-35 | Yellowed within 24 hours. |
| 1,1,5,5-Tetraphenyl-1,3,3,5-Tetramethyltrisiloxane + 0.1 wt % Citric Acid in Distilled Water | 32-35 | No clouding/yellowing after 25 days. Clouding when heat removed but fully recovered within 10 minutes at room temperature or 2 minutes at elevated temperature. |
| 3,5,7-Triphenylnonamethylpentasiloxane + 0.1 wt % Citric Acid in Distilled Water | 32-35 | No clouding/yellowing after 25 days. Clouding when heat removed but fully recovered within 10 minutes at room temperature or 2 minutes at elevated temperature. |

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus the following claims are hereby incorporated into the Detailed Description, with each claim standing on its own as a separately claimed subject matter.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A luminaire, comprising:
a driver circuit;
a plurality of light sources coupled to the driver circuit to emit artificial lighting light in a preselected band within the infrared, visible, or ultraviolet spectrums;
a plurality of electrowetting cells coupled to the plurality of light sources to beam steer or beam shape the artificial lighting from the plurality of light sources;
wherein the plurality of electrowetting cells comprises a conductive fluid and a non-conductive fluid having refractive indices that differ by at least 0.2; and
wherein the conductive fluid and the non-conductive fluid of the plurality of electrowetting cells are capable of providing at least 50% transmissivity with regard to the artificial lighting in the preselected band within the infrared, visible, or ultraviolet spectrums after 1 hour of an exposure at an average illuminance of at least 80,000 lux from the artificial lighting.

2. The luminaire of claim 1, wherein the preselected band comprises at least 5% of the wavelengths within the infrared, visible, or ultraviolet spectrums.

3. The luminaire of claim 1, wherein the preselected band comprises at least 10% of the wavelengths within the infrared, visible, or ultraviolet spectrums.

4. The luminaire of claim 1, wherein the conductive fluid and non-conductive fluid have surface tensions that differ by at least 10 mN/m.

5. The luminaire of claim 1, wherein the non-conductive fluid has a refractive index of at least 1.55.

6. The luminaire of claim 1, wherein the non-conductive fluid is selected from a silicon based fluid, a polyphenyl ether, or a polyphenylene oxide.

7. The luminaire of claim 1, wherein:
the conductive fluid and the non-conductive fluid of the plurality of electrowetting cells are capable of providing at least 60% transmissivity with regard to the artificial lighting after 1 hour of an exposure at an average illuminance of at least 80,000 lux from the artificial lighting.

8. The luminaire of claim 1, wherein:
the conductive fluid and the non-conductive fluid of the plurality of electrowetting cells are capable of providing at least 75% transmissivity with regard to the artificial lighting after 1 hour of an exposure at an average illuminance of at least 80,000 lux from the artificial lighting.

9. The luminaire of claim 1, wherein:
the conductive fluid and the non-conductive fluid of the plurality of electrowetting cells are capable of providing at least 80% transmissivity with regard to the artificial lighting after 1 hour of an exposure at an average illuminance of at least 80,000 lux from the artificial lighting.

10. The luminaire of claim 1, wherein:
the plurality of electrowetting cells include:
a non-transparent substrate that includes a well filled with the conductive fluid and the non-conductive fluid;
a first plate coupled to the non-transparent substrate to seal a top of the well and form a first transparent window at one axial end of the well, the first plate residing in an optical active area through which light is transmitted or reflected; and a second plate coupled to the substrate to seal a bottom of the well and form a second transparent cover window at an opposite axial end of the well, the second plate residing in the optical active area.

11. An electrowetting cell optic comprising:
a driver circuit;
a plurality of electrical-to-optical transducers coupled to the driver circuit to emit artificial lighting in a preselected band within the infrared, visible, or ultraviolet spectrums;
a plurality of electrowetting cells coupled to the plurality of electrical-to-optical transducers to optically change or spatially modulate a light distribution output from the electrical-to-optical transducers;
wherein the plurality of electrowetting cells include a conductive fluid and a non-conductive fluid having refractive indices that differ by at least 0.2; and
wherein the conductive fluid and the non-conductive fluid of the plurality of electrowetting cells are capable of providing at least 50% transmissivity with regard to the artificial lighting after 1 hour of an exposure at an average illuminance of at least 80,000 lux from the artificial lighting.

12. The electrowetting cell optic of claim 11, wherein the preselected band comprises at least 5% of the wavelengths within the x-ray, ultraviolet, visible, infrared, microwave, or radiowave spectrums.

13. The electrowetting cell optic of claim 11, wherein the preselected band comprises at least 10% of the wavelengths within the x-ray, ultraviolet, visible, infrared, microwave, or radiowave spectrums.

14. The electrowetting cell optic of claim 11, wherein the conductive fluid and the non-conductive fluid have surface tensions that differ by at least 10 mN/m.

15. The electrowetting cell optic of claim 11, wherein the non-conductive fluid has a refractive index of at least 1.55.

16. The electrowetting cell optic of claim 11, wherein the non-conductive fluid is selected from a silicon based fluid, a polyphenyl ether, or a polyphenylene oxide.

17. The electrowetting cell optic of claim 11, wherein:
the conductive fluid and the non-conductive fluid of the plurality of electrowetting cells are capable of providing at least 60% transmissivity with regard to the artificial lighting after 1 hour of an exposure at an average illuminance of at least 80,000 lux from the artificial lighting.

18. The electrowetting cell optic of claim 11, wherein:
the conductive fluid and the non-conductive fluid of the plurality of electrowetting cells are capable of providing at least 75% transmissivity with regard to the artificial lighting after 1 hour of an exposure at an average illuminance of at least 80,000 lux from the artificial lighting.

19. The electrowetting cell optic of claim 11, wherein:
the conductive fluid and the non-conductive fluid of the plurality of electrowetting cells are capable of providing at least 80% transmissivity with regard to the artificial lighting after 1 hour of an exposure at an average illuminance of at least 80,000 lux from the artificial lighting.

20. The electrowetting cell optic of claim 11, wherein:
the plurality of electrowetting cells include:
a non-transparent substrate that includes a well filled with the conductive fluid and the non-conductive fluid;
a first plate coupled to the non-transparent substrate to seal a top of the well and form a first transparent window at one axial end of the well, the first plate residing in an optical active area through which light is transmitted or reflected; and
a second plate coupled to the substrate to seal a bottom of the well and form a second transparent cover window at an opposite axial end of the well, the second plate residing in the optical active area.

* * * * *